(12) United States Patent
Navia et al.

(10) Patent No.: US 7,927,371 B2
(45) Date of Patent: Apr. 19, 2011

(54) APPARATUS AND METHOD FOR REDUCING CARDIAC VALVE REGURGITATION

(75) Inventors: Jose Luis Navia, Shaker Heights, OH (US); Jose Antonio Navia, Buenos Aires (AR); Ghassan Kassab, Zionsville, IN (US)

(73) Assignee: The Cleveland Clinic Foundation, Cleveland, OH (US)

( * ) Notice: Subject to any disclaimer, the term of this patent is extended or adjusted under 35 U.S.C. 154(b) by 1089 days.

(21) Appl. No.: 11/586,828

(22) Filed: Oct. 26, 2006

(65) Prior Publication Data
US 2007/0233239 A1   Oct. 4, 2007

Related U.S. Application Data

(63) Continuation-in-part of application No. 11/486,584, filed on Jul. 14, 2006, now abandoned.

(60) Provisional application No. 60/699,730, filed on Jul. 15, 2005.

(51) Int. Cl.
*A61F 2/24* (2006.01)
(52) U.S. Cl. ...................................... 623/2.37; 623/2.36
(58) Field of Classification Search .......... 623/2.1–2.19, 623/2.36, 2.37, 2.38, 2.39, 2.4, 2.41
See application file for complete search history.

(56) References Cited

U.S. PATENT DOCUMENTS

| | | | |
|---|---|---|---|
| 5,824,066 A | 10/1998 | Gross | |
| 6,419,696 B1 | 7/2002 | Ortiz et al. | |
| 6,569,198 B1 | 5/2003 | Wilson et al. | |
| 6,810,882 B2 | 11/2004 | Langberg et al. | |
| 2001/0021874 A1 * | 9/2001 | Carpentier et al. | .......... 623/2.37 |
| 2003/0191528 A1 | 10/2003 | Quijano et al. | |
| 2003/0199974 A1 | 10/2003 | Lee et al. | |
| 2003/0229395 A1 | 12/2003 | Cox | |
| 2004/0138744 A1 | 7/2004 | Lashinski et al. | |
| 2004/0162611 A1 | 8/2004 | Marquez | |

(Continued)

FOREIGN PATENT DOCUMENTS

WO   WO 2004/045463 A2   6/2004

(Continued)

OTHER PUBLICATIONS

Ernst et al., Initial Experience with Remote Catheter Ablation Using a Novel Magnetic Navigation System, *Circulation*, 2004; 109:1472-1475.

(Continued)

*Primary Examiner* — David Isabella
*Assistant Examiner* — Suba Ganesan
(74) *Attorney, Agent, or Firm* — Tarolli, Sundheim, Covell & Tummino LLP

(57) ABSTRACT

An apparatus for modifying the annulus of a cardiac valve to reduce regurgitation of blood flow through the cardiac valve includes a first annuloplasty ring having a first diameter and being disposed about a first aspect of the annulus of the cardiac valve. The apparatus also includes an elongate flexible body having proximal and distal end portions and being insertable into the first annuloplasty ring. The elongate flexible body has an adjustable mechanism for selectively adjusting the elongate flexible body from a first relaxed configuration to a second tensioned configuration. The first annuloplasty ring is adaptable to obtain a second smaller diameter and to cause the annulus of the cardiac valve to be modified and reduce regurgitation of blood flow through the cardiac valve when the elongate flexible body obtains the second tensioned configuration.

13 Claims, 24 Drawing Sheets

U.S. PATENT DOCUMENTS

| | | |
|---|---|---|
| 2004/0167620 A1 | 8/2004 | Ortiz et al. |
| 2004/0225353 A1 | 11/2004 | McGuckin, Jr. et al. |
| 2004/0236419 A1 | 11/2004 | Milo |
| 2004/0243227 A1 | 12/2004 | Starksen et al. |
| 2005/0033446 A1 | 2/2005 | Deem et al. |
| 2005/0055087 A1 | 3/2005 | Starksen |
| 2005/0137700 A1 | 6/2005 | Spence et al. |
| 2005/0197696 A1 | 9/2005 | Gomez Duran |
| 2005/0267571 A1* | 12/2005 | Spence et al. ............ 623/2.36 |
| 2005/0288776 A1 | 12/2005 | Shaoulian et al. |
| 2005/0288781 A1 | 12/2005 | Moaddeb et al. |
| 2006/0015178 A1 | 1/2006 | Moaddeb et al. |
| 2006/0041306 A1 | 2/2006 | Vidlund et al. |
| 2006/0069429 A1 | 3/2006 | Spence et al. |
| 2006/0116757 A1 | 6/2006 | Lashinski et al. |
| 2006/0184242 A1 | 8/2006 | Lichtenstein |

FOREIGN PATENT DOCUMENTS

| | | |
|---|---|---|
| WO | WO 2004/045463 A3 | 6/2004 |
| WO | WO 2005/046488 A2 | 5/2005 |
| WO | WO 2005/046488 A3 | 5/2005 |
| WO | WO 2006/012038 A2 | 2/2006 |

OTHER PUBLICATIONS

Noar et al., Rare Earth Magnets in Orthodontics: An Overview, *British Journal of Orthodonitics*, 1999;26:29-37.

* cited by examiner

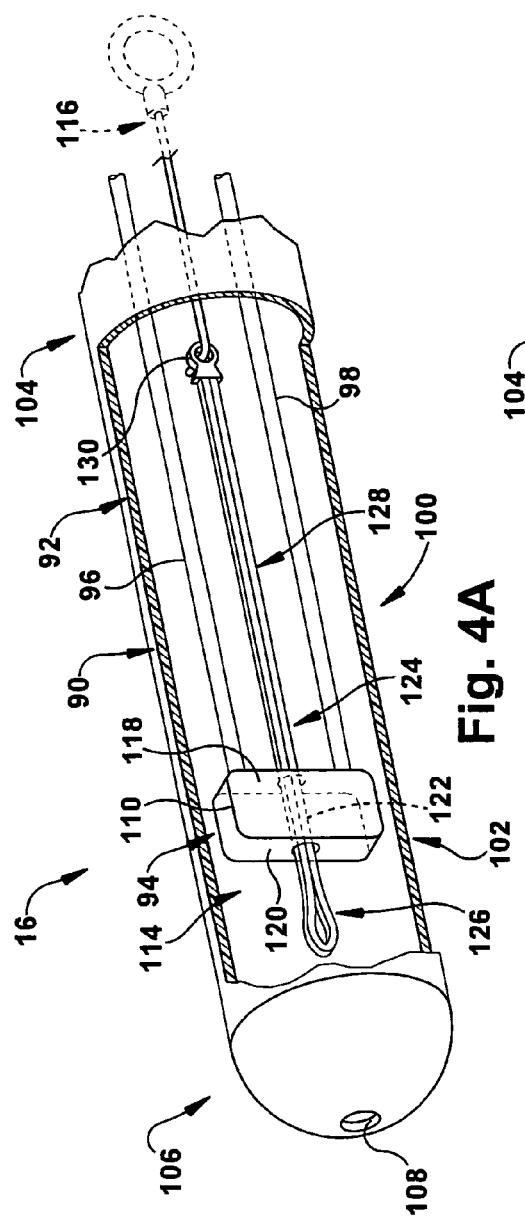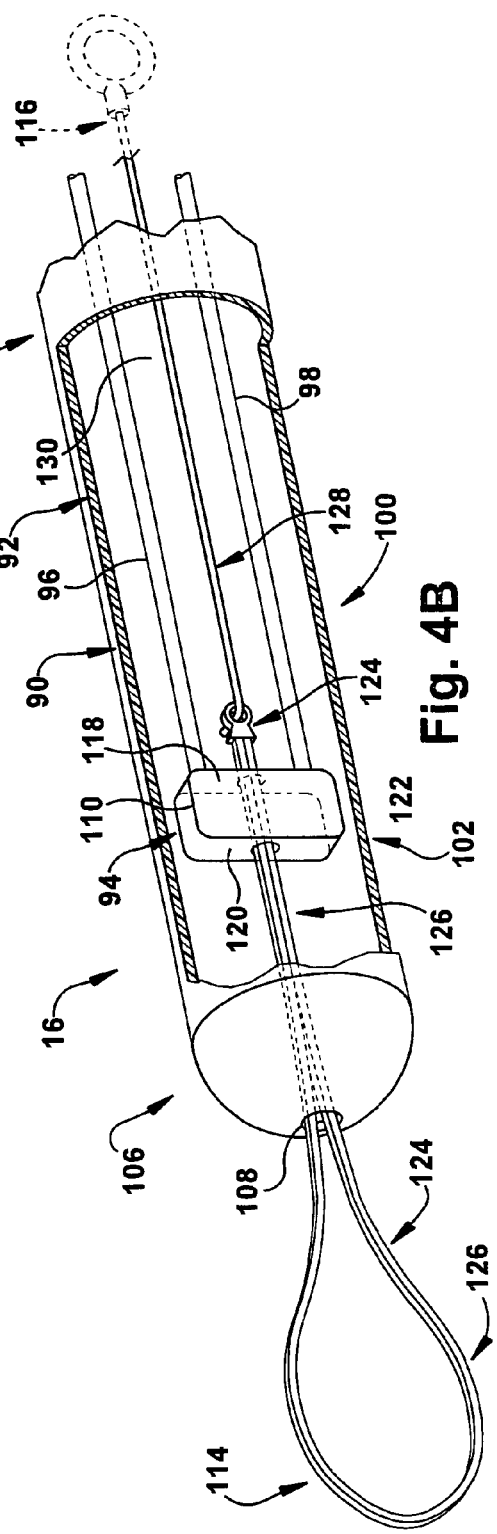

APPARATUS AND METHOD FOR REDUCING CARDIAC VALVE REGURGITATION

RELATED APPLICATIONS

This application is a continuation-in-part of U.S. patent application Ser. No. 11/486,584, filed Jul. 14, 2006 now abandoned, which claims priority from U.S. Provisional Patent Application Ser. No. 60/699,730, filed Jul. 15, 2005. The subject matter of the aforementioned applications is incorporated herein by reference in their entireties.

TECHNICAL FIELD

The present invention relates generally to an apparatus and method for treating cardiac valve insufficiencies, and more particularly to an apparatus and method for reducing or preventing regurgitation of blood flow through a cardiac valve.

BACKGROUND OF THE INVENTION

Mitral and tricuspid valve replacement and repair are traditionally performed with suture techniques. During valve replacement, sutures are spaced around the annulus (the point where the valve leaflet attaches to the heart) and then the sutures are attached to a prosthetic valve. The valve is lowered into position and when the sutures are tied, the valve is fastened to the annulus. The surgeon may remove all or part of the valve leaflets before inserting the prosthetic valve. In valve repair, a diseased valve is left in situ and surgical procedures are performed to restore its function.

Frequently, an annuloplasty ring is used to reduce the size of the annulus. The ring serves to reduce the diameter of the annulus by allowing the leaflets to oppose each other normally and prevent re-dilation of the annulus. Sutures are used to attach a prosthetic ring to the annulus and to assist in plicating the annulus. This procedure, like heart valve replacement, is time-consuming. If the ring is severely malpositioned, then the stitches must be removed and the ring repositioned relative to the valve annulus during restitching. In other cases, a less than optimum annuloplasty may be tolerated by the surgeon rather than lengthening the time of surgery to restitch the ring.

SUMMARY OF THE INVENTION

In one aspect of the present invention, an apparatus for modifying the annulus of a cardiac valve to reduce regurgitation of blood flow through the cardiac valve comprises a first annuloplasty ring having a first diameter and being disposed about a first aspect of the annulus of the cardiac valve, and an elongate flexible body comprising proximal and distal end portions and being insertable into the first annuloplasty ring. The elongate flexible body includes an adjustable mechanism for selectively adjusting the elongate flexible body from a first relaxed configuration to a second tensioned configuration. The first annuloplasty ring is adaptable to obtain a second smaller diameter and to cause the annulus of the cardiac valve to be modified and reduce regurgitation of blood flow through the cardiac valve when the elongate flexible body obtains the second tensioned configuration.

In another aspect of the present invention, a method is provided for modifying the annulus of a cardiac valve to reduce regurgitation of blood flow through the cardiac valve. An apparatus comprising a first annuloplasty ring and an elongate flexible body is first provided. The first annuloplasty ring having a first diameter and is disposed about a first aspect of the annulus of the cardiac valve. The elongate flexible body has proximal and distal end portions and is insertable into the first annuloplasty ring. The elongate flexible body includes an adjustable mechanism for selectively adjusting the elongate flexible body from a first relaxed configuration to a second tensioned configuration. The elongate flexible body is then inserted into the first annuloplasty ring in the first relaxed configuration. Next, the adjustment mechanism is manipulated so that the elongate flexible body obtains the second tensioned configuration and causes the first annuloplasty ring to obtain a second smaller diameter, thereby modifying the annulus of the cardiac valve and reducing regurgitation of blood flow through the cardiac valve. The elongate flexible body is then removed from the first annuloplasty ring.

In another aspect of the present invention, an apparatus for modifying the annulus of a cardiac valve to reduce regurgitation of blood flow through the cardiac valve comprises a first annuloplasty ring having a first diameter and being disposed about a first aspect of the annulus of the cardiac valve, and a flexible body comprising first and second oppositely disposed strut members having proximal and distal end portions. The flexible body additionally includes a cinching mechanism for adjusting the flexible body from a first relaxed configuration to a second tensioned configuration. The cinching mechanism is operatively connected to the distal end portion of the strut members. The cinching mechanism comprises a resistance member operatively coupled to the distal end portion of the strut members, and a harness member operatively coupled to a pull wire extending between the strut members. The flexible body is disposed in a delivery catheter that is insertable into the first annuloplasty ring. The delivery catheter comprises proximal and distal end portions and an opening at the distal portion for extending the harness member therethrough. The flexible body is adaptable to obtain the second tensioned configuration and to cause the first annuloplasty ring to obtain a second smaller diameter so that the annulus of the cardiac valve is modified and regurgitation of blood flow through the cardiac valve is reduced.

In another aspect of the present invention, a method is provided for modifying the annulus of a cardiac valve to reduce regurgitation of blood flow through the cardiac valve. An apparatus comprising a first annuloplasty ring and a flexible body is first provided. The first annuloplasty ring has a first diameter and is disposed about a first aspect of the annulus of the cardiac valve. The flexible body comprises first and second oppositely disposed strut members having proximal and distal end portions and a cinching mechanism for adjusting the flexible body from a first relaxed configuration to a second tensioned configuration. The cinching mechanism comprises a resistance member operatively coupled to the distal end portion of the strut members and a harness member operatively coupled to a pull wire extending between the strut members. The flexible body is disposed in a delivery catheter comprising proximal and distal end portions and an opening at the distal portion for extending the harness member therethrough. The flexible body is inserted into the first annuloplasty ring in the first relaxed configuration, and the cinching mechanism then manipulated so that the first annuloplasty ring obtains a second smaller diameter and modifies the annulus of the cardiac valve to reduce regurgitation of blood flow through the cardiac valve. The flexible body is then removed the first annuloplasty ring.

In another aspect of the present invention, an apparatus for modifying the annulus of a cardiac valve to reduce regurgitation of blood flow through the cardiac valve comprises a first annuloplasty ring having a first diameter and being disposed about a first aspect of the annulus of the cardiac valve, and an electromagnetic wire having proximal and distal end portions. The electromagnetic wire includes a plurality of magnetic members operably connected to the electromagnetic wire and an adjustable mechanism for selectively adjusting the electromagnetic wire from a first relaxed configuration to a second tensioned configuration. The electromagnetic wire is insertable into the first annuloplasty ring. The adjustable mechanism is selectively adjustable so that the first annuloplasty ring is adaptable to obtain a second smaller diameter and modify the annulus of the cardiac valve to reduce regurgitation of blood flow through the cardiac valve.

In another aspect of the present invention, a method is provided for modifying the annulus of a cardiac valve to reduce regurgitation of blood flow through the cardiac valve. An apparatus comprising a first annuloplasty ring and an electromagnetic wire is first provided. The first annuloplasty ring has a first diameter and is disposed about a first aspect of the annulus of the cardiac valve. The electromagnetic wire has proximal and distal end portions and includes a plurality of magnetic members operably connected to the electromagnetic wire. The electromagnetic wire also includes an adjustable mechanism for selectively adjusting the electromagnetic wire from a first relaxed configuration to a second tensioned configuration. The electromagnetic wire is inserted the electromagnetic wire into the first annuloplasty ring in the first relaxed configuration, and the adjustable mechanism is then manipulated so that the electromagnetic wire obtains the second tensioned configuration and the first annuloplasty ring obtains a second smaller diameter to modify the annulus of the cardiac valve and reduce regurgitation of blood flow through the cardiac valve. The electromagnetic wire is then removed from the first annuloplasty ring.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 4A is a perspective view showing an alternative embodiment of the apparatus shown in FIG. 1 comprising a flexible body having a harness member in a collapsed configuration;

FIG. 4B is a perspective view of the flexible body shown in FIG. 4A with the harness member having an open configuration;

DETAILED DESCRIPTION

Figure 1:
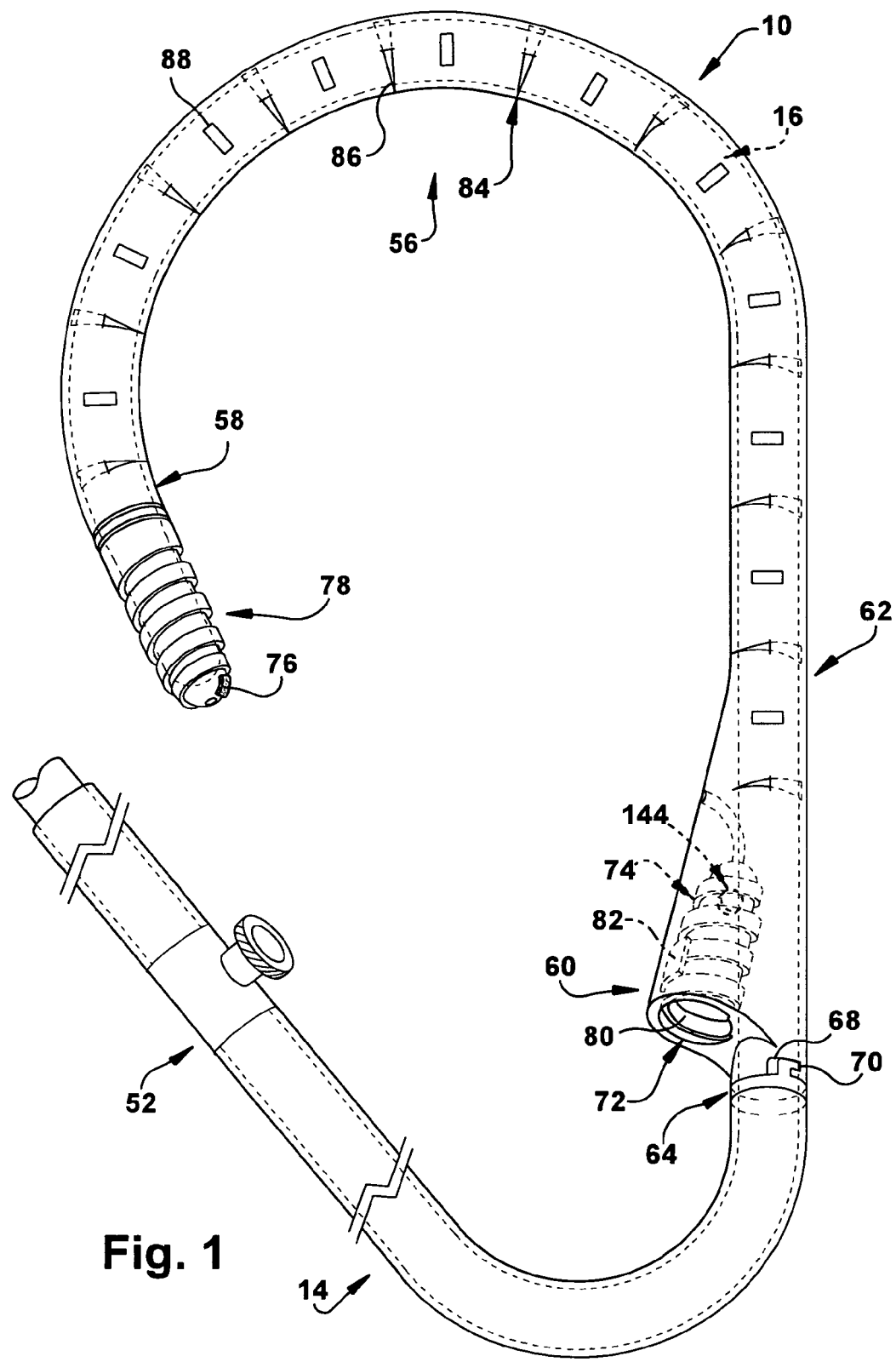
FIG. 1 is a perspective view of an apparatus for reducing cardiac valve regurgitation constructed in accordance with the present invention.

The present invention relates generally to an apparatus and method for treating cardiac valve insufficiencies, and more particularly to an apparatus and method for reducing or preventing regurgitation of blood flow through a cardiac valve. As representative of the present invention, FIG. 1 illustrates an apparatus 10 for modifying a cardiac valve 12 (FIG. 2) comprising a first annuloplasty ring 14 (FIG. 1) and an elongate flexible body 16. The elongate flexible body 16 is insertable into the first annuloplasty ring 14 and may be adjusted so that the annulus 18 of the cardiac valve 12 (FIG. 2) is modified and regurgitation of blood flow through the cardiac valve is reduced or eliminated.

Figure 2:
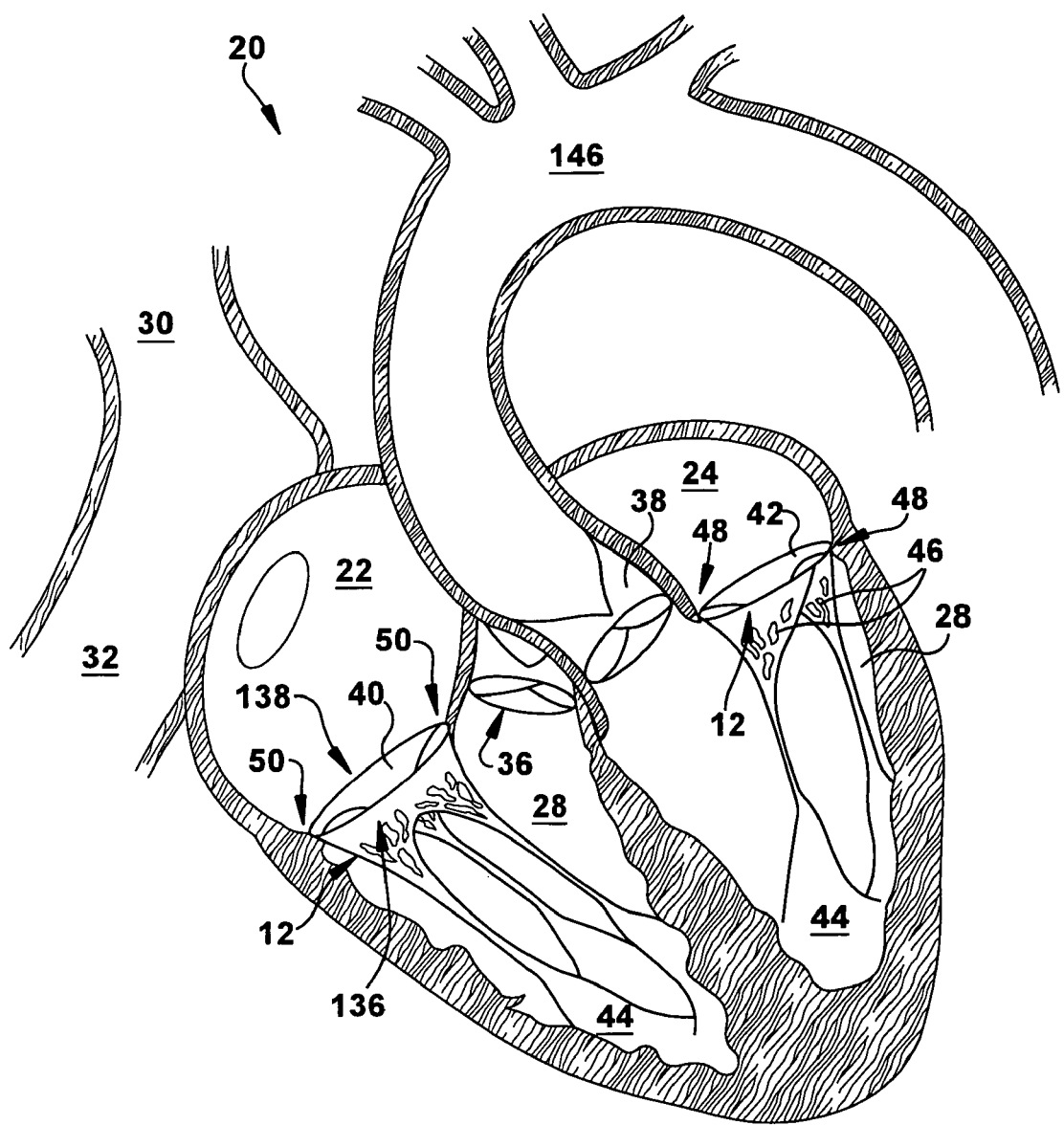
FIG. 2 is a cross-sectional schematic view of a human heart.
Figure 20:
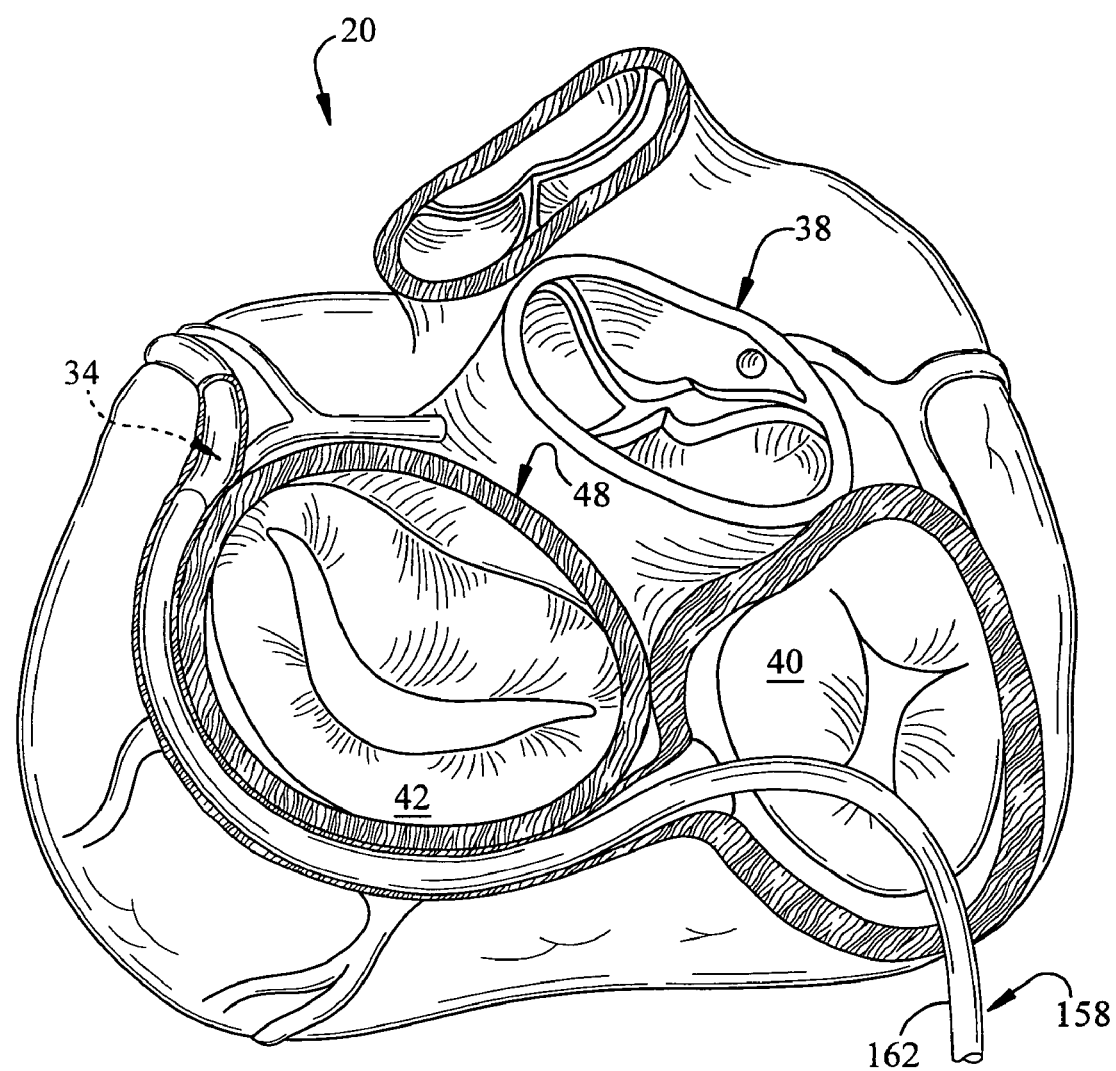
FIG. 20 is a perspective view of a human heart showing a positioning catheter implanted in the coronary sinus of the heart.

FIG. 2 shows a human heart 20. The human heart 20 contains four chambers: the right and left atria 22 and 24 and the right and left ventricles 26 and 28. The thin-walled right atrium 22 receives deoxygenated blood from the superior vena cava 30, the inferior vena cava 32, and from the coronary sinus 34 (FIG. 20). The thin-walled left atrium 24 (FIG. 2) receives oxygenated blood from pulmonary veins (not shown). The left and right ventricles 28 and 26 pump oxygenated and deoxygenated blood, respectively, throughout the body, and the pocket-like pulmonary and aortic semilunar valves 36 and 38 prevent reflux into the ventricles. Atrial blood is pumped through the atrioventricular orifices, guarded by the 3-cusp tricuspid valve 40 on the right and the 2-cusp mitral valve 42 on the left. The mitral and tricuspid valves 42 and 40 are secured to the papillary muscles 44 in the left and right ventricles 28 and 26 by tendinous chordae tendineae 46 and by the mitral and tricuspid valve annuluses 48 and 50, areas of heart wall tissue at the junction of the atrial and ventricular walls that are relatively fibrous and significantly stronger than leaflet tissue.

Figure 3:
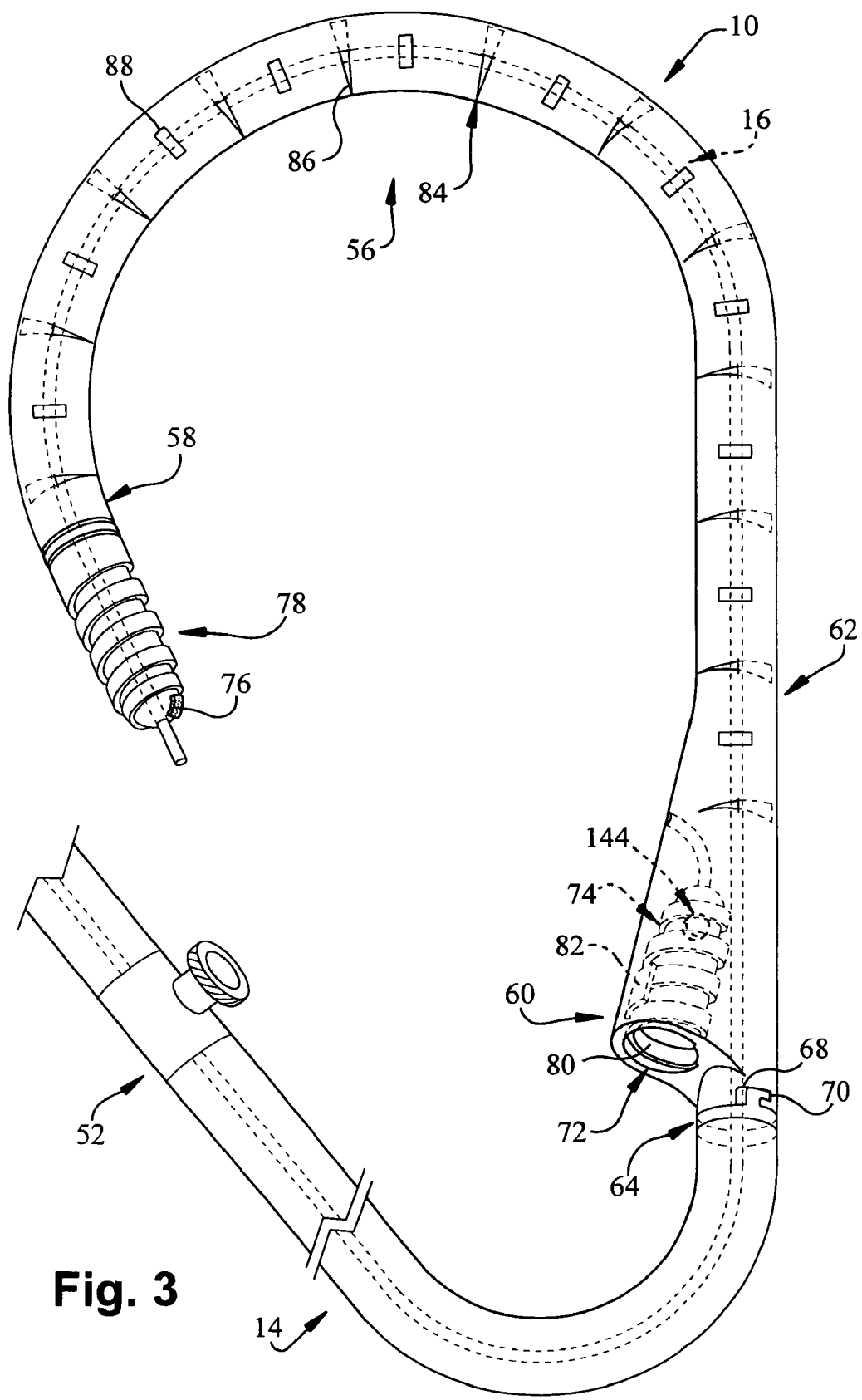
FIG. 3 is a perspective view showing a first annuloplasty ring of the apparatus shown in FIG. 1.

As shown in FIG. 3, the first annuloplasty ring 14 comprises a catheter ring (or sheath) 52 and a wire catheter (or guide) 54 disposed within the catheter ring. The catheter ring 52 may be flexible or rigid. For example, the catheter ring 52 may be comprised of multiple segments (not shown) configured such that the catheter ring is deformable by tensioning a tensioning member (not shown) coupled to the segments. Alternatively, the catheter ring 52 may be formed from an elastic material having a geometry selected to engage and optionally shape or constrict the annulus 18 of the cardiac valve 12. For instance, the catheter ring 52 may be formed from super-elastic material, shape memory alloy such as Nitinol, spring stainless steel, or the like. In other instances, the catheter ring 52 can be made of a rigid material such as hardened plastic, silicon, polyurethane, or the like. Alternatively, the catheter ring 52 may be selectively rigidified in situ, such as with a gooseneck or lockable element shaft (not shown), or any other rigidifying structure.

A distal end portion 56 of the first annuloplasty ring 14 includes a terminal end 58 a connecting section 60 spaced apart by a predetermined length 62. The connecting section 60 includes means 64 for disconnecting from a main body portion 66. For instance, the means 64 for disconnecting from the main body portion 66 can comprise first and second ring members 68 and 70 respectively attached to the connecting section 60 and the main body portion. The first ring member 68 can have a female portion (not shown in detail) capable of mating with a male portion (not shown in detail) of the second ring member 70. When separation of the connecting section 60 from the main body portion 66 is desired, the main body portion, the connecting section, or both can be rotated or unlocked so that the male portion of the second ring member 70 is displaced from and thus no longer mated to the female portion of the first ring member 68.

Alternative means 64 for disconnecting from the main body portion 66 are also possible. For instance, the means 64 for disconnecting can comprise at least two magnetic members (not shown) each securely attached to the connecting section 60 and the main body portion 66. When appropriately positioned, the magnetic members may be magnetically attracted so that the connecting section 60 and the main body portion 66 are joined. Then, when an appropriate amount of force (e.g., torque) is applied to the main body portion 66, the connecting section 60, or both, the magnetic members may be sufficiently distanced so that the connecting section and the main body portion are separated.

The connecting section 60 further includes means 72 for interconnecting with the terminal end 58. As shown in FIG. 3, the means 72 for interconnecting with the terminal end 58 can include a receptacle portion 74. The receptacle portion 74 has a shape complementary to the shape of the terminal end 58 such that the receptacle portion is capable of mating with the terminal end. Additionally, the receptacle portion 74 can include at least one first magnet 76.

As is also shown in FIG. 3, the terminal end 58 may have a shape complementary to the shape of the receptacle portion 74 such that the terminal end is capable of mating with the receptacle portion. For instance, the terminal end 58 may include a threaded portion 78 capable of mating with the receptacle portion 74 (which may also have a threaded portion 80 complementary in shape to the terminal end). Additionally, the terminal end 58 may include at least one second magnet 82.

The distal end portion 56 of the first annuloplasty ring 14 includes means 84 for attaching to the annulus 18 of the cardiac valve 12. The means 84 for attaching comprises a plurality of deployable hook members 86. The deployable hook members 86 can include any type of fastener, including, for example, C-shaped or semicircular hooks, curved hooks of other shapes, straight hooks, barbed hooks, clips of any kind, T-tags, or any other suitable fastener. The deployable hook members 86 may be made of any suitable material, such as super-elastic or shape-memory material like Nitinol or spring stainless steel. Additionally, the deployable hook members 86 may be made of a magnetic or electromagnetic material such as iron, NdFeB, SmCo and Alnico.

Figure 9A:
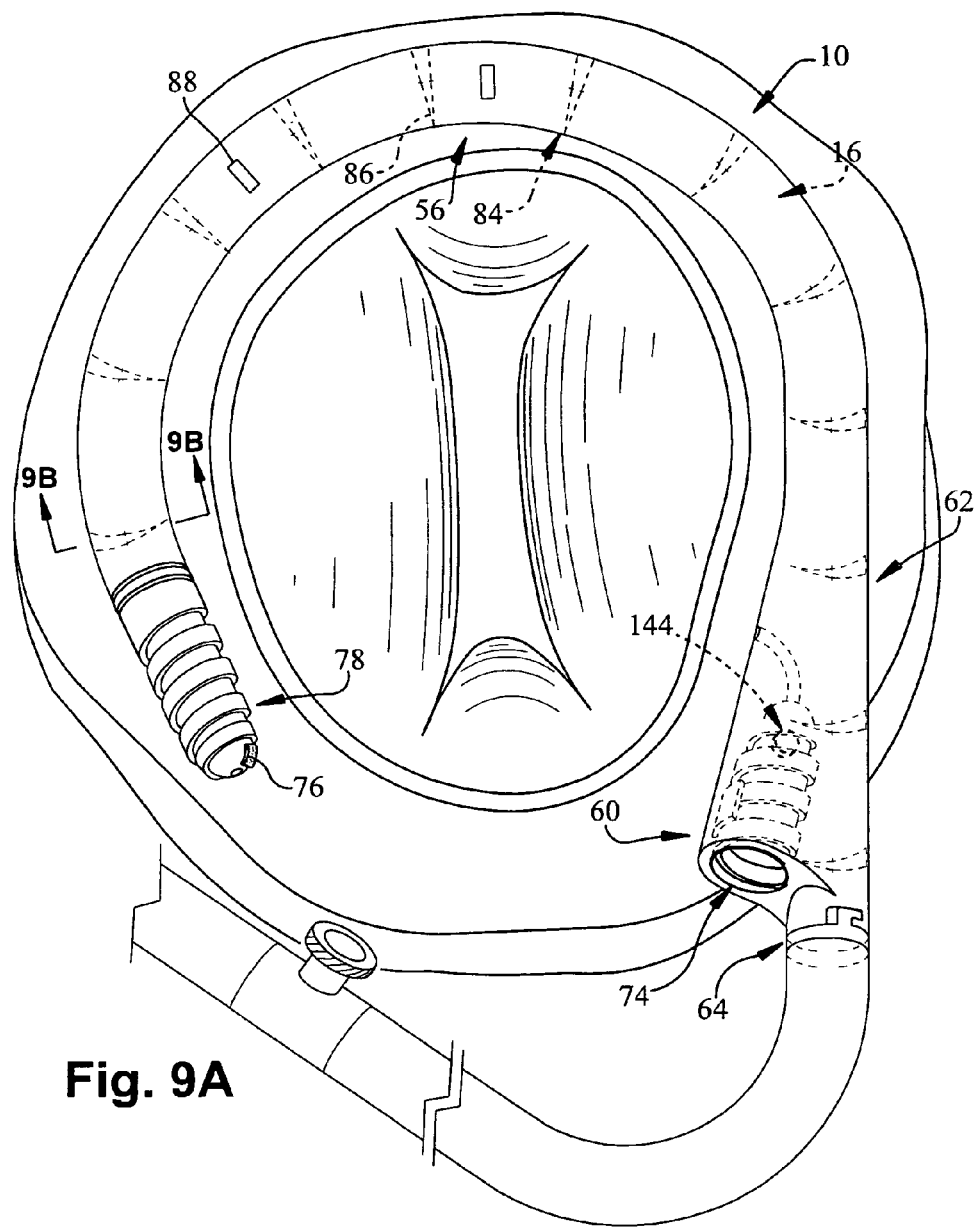
FIG. 9A is a perspective view showing the apparatus in FIG. 3 disposed about a superior aspect of the mitral valve annulus.
Figure 9B:
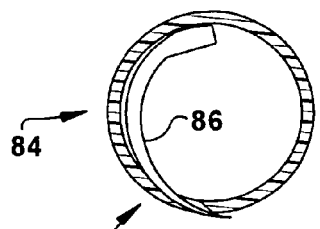
FIG. 9B is a sectional view along line 9B-9B in FIG. 9A showing deployable hook members having a non-deployed configuration.
Figure 9C:
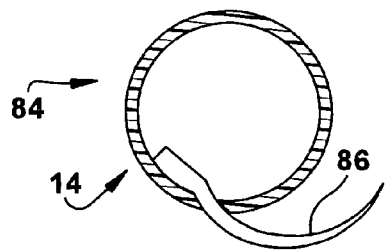
FIG. 9C is a sectional view showing deployable hook members in FIG. 9B having a deployed configuration.

The deployable hook members 86 are integrally secured to the distal end portion 56. By "deployable" it is meant that the deployable hook members 86 can change from a first non-deployed shape (FIG. 9B) to a second deployed shape (FIG. 9C). When deployed, the deployable hook members 86 may change shape, enter the annulus 18 of the cardiac valve 12, and attach to the annulus of the cardiac valve. Thus, a crimping device or other similar mechanism is not required on the distal end portion 56 (FIG. 3) to apply force to the deployable hook members 86 and attach the deployable hook members to the annulus 18 of the cardiac valve 12.

The distal end portion 56 of the first annuloplasty ring 14 may additional include at least one magnetic element 88. The magnetic element 88 may be comprised of a ferromagnetic material, such as Fe—C or Fe—Pd, and may be securely disposed about the distal end portion 56 of the first annuloplasty ring 14. The magnetic element 88 may be magnetically attracted to magnetic elements located on other implantable structures, such as other annuloplasty rings, for example.

Although the first annuloplasty ring 14 is shown having a circular cross-sectional shape in FIG. 3, the first annuloplasty ring may have any other suitable shape. For example, it may be advantageous to provide a first annuloplasty ring 14 having an ovoid or elliptical cross-sectional shape (not shown). Such a shape may help ensure that the first annuloplasty ring 14 is aligned, when positioned in a corner formed by a ventricular wall and a valve leaflet, so that the distal end portion 56 is optimally oriented to deliver the deployable hook members 86 into the annulus 18 of the cardiac valve 12. To further enhance contacting to the annulus 18 of the cardiac valve 12 and/or orientation of the first annuloplasty ring 14, an expandable member (not shown) may also be coupled to the first annuloplasty ring which expands to urge or press the first annuloplasty ring into the corner formed by the ventricle wall and the valve leaflet.

One embodiment of the present invention is illustrated in FIGS. 4A and 4B. As shown in FIG. 4A, an apparatus 10 for modifying the annulus 18 of a cardiac valve 12 comprises a flexible body 90 having proximal and distal end portions 92 and 94. The flexible body 90 is comprised of oppositely disposed first and second strut members 96 and 98 operably coupled to a cinching mechanism 100. The first and second strut members 96 and 98 have a thin, wire-like configuration and are comprised of a flexibly resilient material, such as Nitinol or stainless steel.

The flexible body 90 is disposed in a delivery catheter 102 having proximal and distal end portions 104 and 106. The delivery catheter 102 is shaped to facilitate insertion and removal of the delivery catheter into and out of the first annuloplasty ring 14. The delivery catheter 102 may be constructed from a rigid, semi-rigid, or flexible material. For example, the delivery catheter 102 may be made of a flexible elastic material, such as a shape memory alloy or super-elastic material (e.g., Nitinol, spring stainless steel, or the like). Alternatively, the delivery catheter 102 may be made of a rigid material such as hardened plastic, silicon, polyurethane, or the like. As shown in FIG. 4A, the distal end portion 106 of the delivery catheter 102 has an opening 108 to facilitate operation of the cinching mechanism 100.

The cinching mechanism 100 is positioned at the distal end portion 106 of the delivery catheter 102. The cinching mechanism 100 comprises a resistance member 110 operatively coupled to the distal end portion 112 of each of the first and second strut members 96 and 98, and a harness member 114 for contacting at least a portion of the first annuloplasty ring 14. The harness member 114 is operatively coupled to a pull wire 116 which extends between the first and second strut members 96 and 98. The pull wire 116 may be comprised of a flexible, semi-flexible, or rigid material, such as Nitinol, stainless steel, plastic polymer, or the like. As described in more detail below, the pull wire 116 is manipulated to adjust the flexible body 90 from a first relaxed configuration to a second tensioned configuration.

The resistance member 110 of the flexible body 90 is coupled to the distal end portion 112 of each of the first and second strut members 96 and 98. The resistance member 110 provides resistance against the first and second strut members 96 and 98 when the pull wire 116 is manipulated, i.e., withdrawn. One example of the resistance member 110 is illustrated in FIGS. 4A and 4B. The resistance member 110 has a block-like configuration with first and second sides 118 and 120. A channel 122 through which the harness member 114 extends is disposed between the first and second sides 118 and 120. The first side 118 of the resistance member 110 is operatively coupled to the distal end portion 112 of each of the first and second strut members 96 and 98. The resistance member 110 may be made of any rigid or semi-rigid material, such as hardened plastic or rubber. It should be appreciated that the resistance member 110 can have any shape or configuration, and is not limited to the block-like configuration illustrated in FIGS. 4A and 4B.

The harness member 114 can extend through the channel 122 of the resistance member 110 to provide a means for contacting a portion of the first annuloplasty ring 14. As shown in FIGS. 4A and 4B, the harness member 114 can comprise an adjustable loop member 124 having distal and proximal end portions 126 and 128 (FIG. 4B). The proximal end portion 128 of the loop member 124 is operatively connected to the pull wire 116 via a connecting ring 130 or other similar device. The loop member 124 may be made of a flexible or semi-flexible material, such as a medical grade suture, stainless steel, or Nitinol. The loop member 124 may be adjusted between a collapsed configuration (FIG. 4A) and an open configuration (FIG. 4B).

The pull wire 116 is used to adjust the configuration of the loop member 124. For example, when the pull wire 116 is withdrawn as in FIG. 4A, the proximal end portion 128 of the loop member 124 is pulled through the channel 122 of the resistance member 110. As the proximal end portion 128 of the loop member 124 is threaded through the channel 122, the distal end portion 126 of the loop member is progressively collapsed. When a radial force is applied to the pull wire 116 as in FIG. 4B, the distal and proximal end portions 126 and 128 of the loop member 124 are progressively threaded through the opening 108 of the delivery catheter 102 and the channel 122 (respectively). As the distal end portion 126 is exuded from the opening 108, the distal end portion of the loop member 124 is expanded and obtains the open configuration.

Figure 5A:
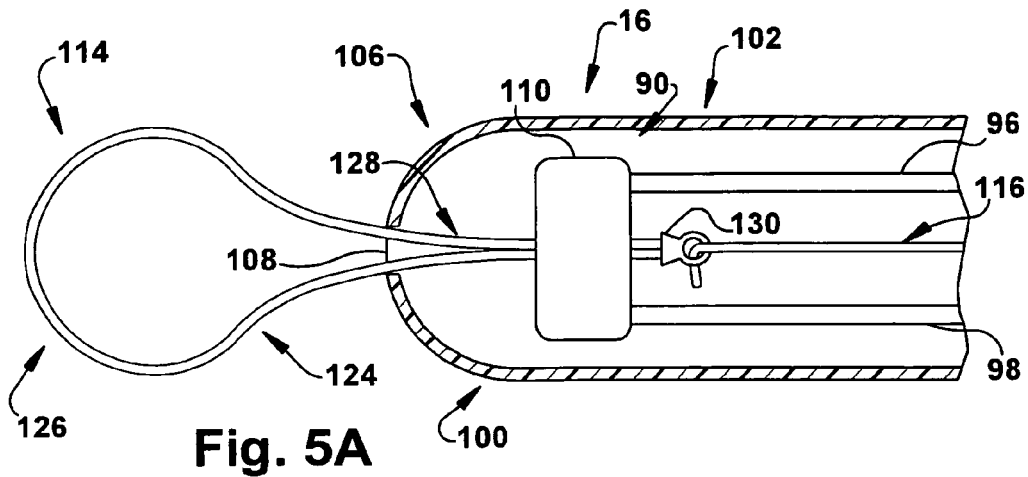
FIG. 5A is a magnified cross-sectional view of the flexible body shown in FIG. 4B showing one configuration of a proximal end portion of the harness member.
Figure 5B:
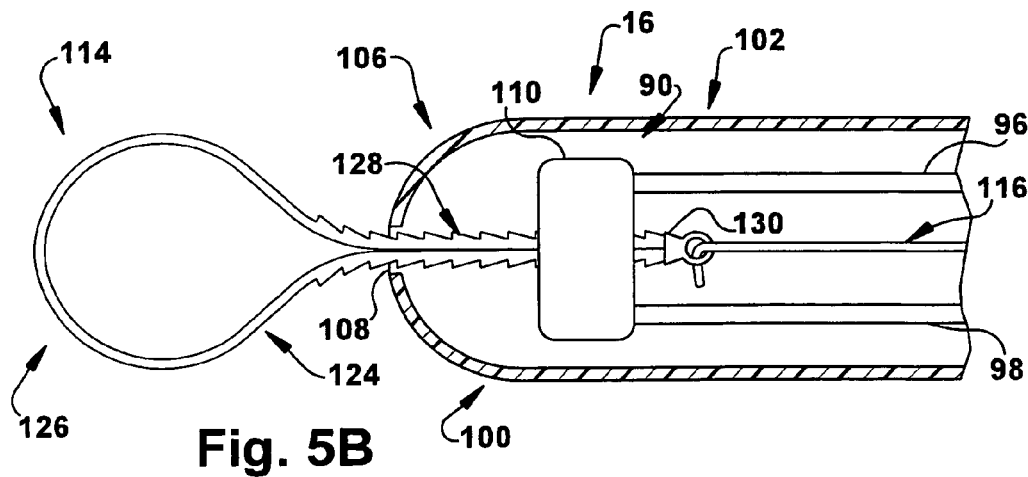
FIG. 5B is a magnified cross-sectional view of the flexible body shown in FIG. 5A showing another configuration of the proximal end portion of the harness member.
Figure 5C:
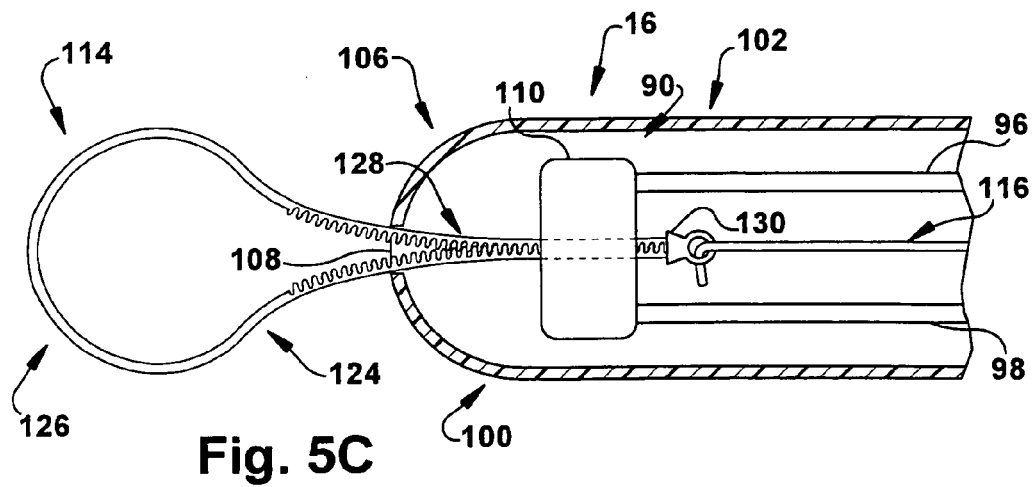
FIG. 5C is a magnified cross-sectional view of the flexible body shown in FIG. 5B showing yet another configuration of the proximal end portion of the harness member.

As shown in FIGS. 5A-C, the proximal end portion 128 of the loop member 124 can comprise a variety of configurations to facilitate movement of the loop member through the channel 122. In FIG. 5A, for example, the proximal end portion 128 of the loop member 124 is comprised of oppositely disposed strands 132. When the pull wire 116 is withdrawn, the strands 132 are progressively meshed together as the strands move through the channel 122 and, in turn, reduce the size of the distal end portion 126 of the loop member 124. The proximal end portion 128 of the loop member 124 can also comprise a click-and-groove mechanism (not shown in detail) as shown in FIG. 5B. When the pull wire 116 is withdrawn, the click-and-groove mechanism is progressively ratcheted through the channel 122 of the resistance member 110 to reduce the size of the distal end portion 126 of the loop member 124. The proximal end portion 128 can additionally comprise a zipper-like mechanism (not shown in detail) as illustrated in FIG. 5C. When the pull wire 116 is withdrawn, the teeth of the zipper mechanism are progressively mated and the size of the distal end portion 126 of the loop member 124 is progressively reduced.

It should be appreciated that the harness member 114 can have a variety of configurations other than the loop member 124 illustrated in FIGS. 4A and 4B. For example, the harness member 114 may comprise a deformable member (not shown), such as a deformable hook or clip, made of a shape memory alloy or other like material. The deformable member may have a linear native conformation and may be selectively extended and retracted through the opening 108 of the delivery catheter 102. When the deformable member is extended from the delivery catheter 102, the deformable member may be modified by delivering energy (e.g., thermal or electromagnetic energy) to the deformable member. Delivering energy to the deformable member may cause the deformable member to obtain an arcuate configuration adapted for contacting a portion of the first annuloplasty ring 14.

As will be discussed in greater detail below, the cinching mechanism 100 may be manually manipulated (i.e., by adjusting the pull wire 116) to adjust the flexible body 90 from a first relaxed configuration to a second tensioned mechanism. By "first relaxed configuration," it is meant that little or no manual force has been applied to the pull wire 116 of the flexible body 90. Consequently, the flexible body 90 obtains a pliable or malleable configuration to facilitate placement of the flexible body in the first annuloplasty ring 14. By "second tensioned configuration," it is meant that some manual force has been applied to the pull wire 116 so that the flexible body 90 obtains a rigid or semi-rigid configuration to facilitate modification of the first annuloplasty ring 14. By placing the flexible body 90 into the first annuloplasty ring 14 in the first relaxed configuration and then adjusting the cinching mechanism 100, the flexible body obtains the second tensioned configuration and thereby modifies the first annuloplasty ring to reduce regurgitation of blood flow through the cardiac valve 12.

Figure 6A:
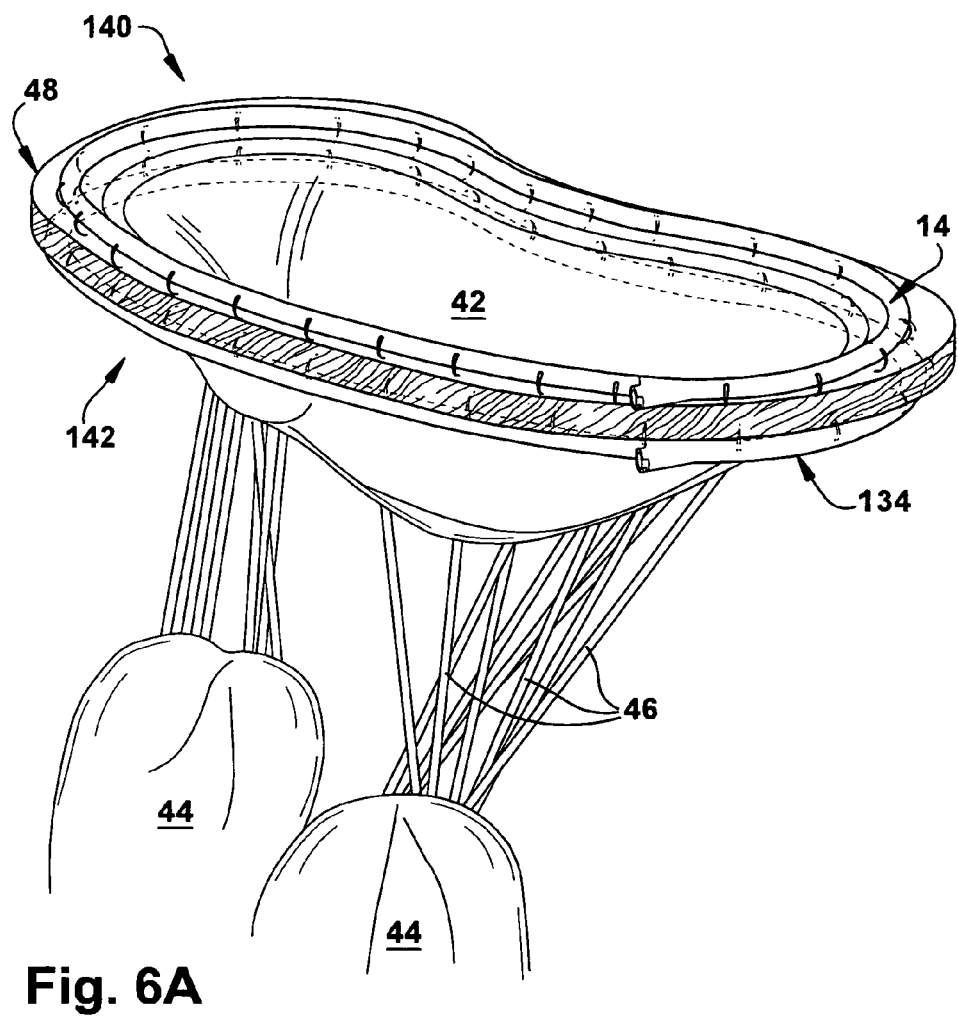
FIG. 6A is a perspective view showing another embodiment of the apparatus shown in FIG. 1 disposed about a mitral valve.
Figure 6B:
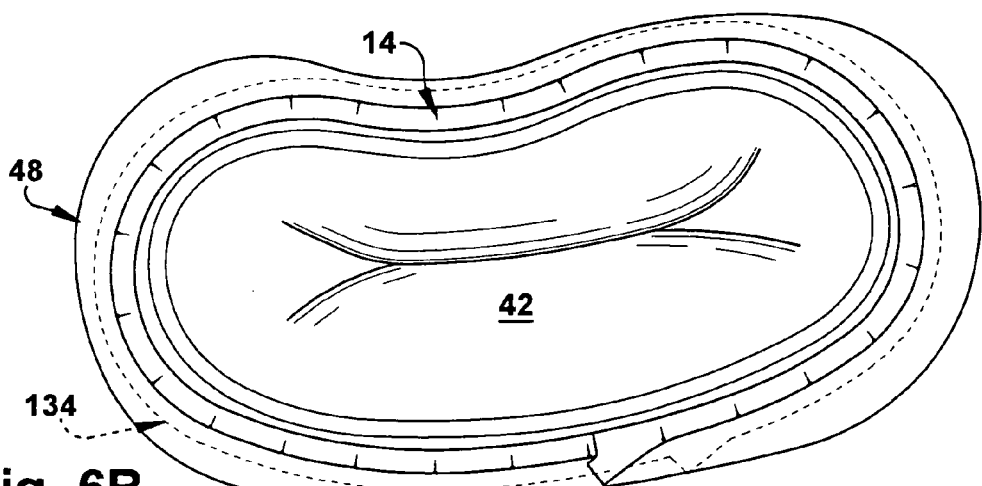
FIG. 6B is a plan view showing the embodiment of the apparatus shown in FIG. 6A disposed about a superior aspect of the mitral valve.

A second embodiment of the present invention is illustrated in FIGS. 6A and 6B and comprises a flexible body 90, a first annuloplasty ring 14, and a second annuloplasty ring 134. The second annuloplasty ring 134 may be disposed about a second aspect 136 of the cardiac valve annulus 18 to facilitate positioning of the first annuloplasty ring 14. As shown in FIG. 6A, the second annuloplasty ring 134 may be identically constructed as the first annuloplasty ring 14. Alternatively, the second annuloplasty ring 134 can comprise any other type of annuloplasty ring known in the art. For example, the second annuloplasty ring 134 can have an annular shape or configuration which is partial (i.e., has an open configuration) or continuous (i.e., has a closed configuration). The second annuloplasty ring 134 can include flexible, semi-rigid and rigid devices having shapes which are circular, D-shaped, C-shaped, saddle-shaped and any other annular or non-annular shape suitable for repairing cardiac valves. The second annuloplasty ring 134 may additionally comprise at least one magnetic element (not shown) to facilitate positioning of the first annuloplasty ring 14.

The present invention also provides a percutaneous method for modifying the annulus 18 of a cardiac valve 12 to reduce regurgitation of blood flow through the cardiac valve. In one embodiment of the method, a first step comprises accessing the annulus 18 of the cardiac valve 12 and measuring the dimensions of the annulus. Access to the annulus 18 may be accomplished by any available technique, including intravascular (described below), transthoracic, and the like. The method of the present invention will typically entail gaining access to a beating heart 20; however, the present invention may also be used for intravascular stopped-heart access as well as stopped-heart open chest procedures.

Prior to use of the apparatus 10, the dimensions of the cardiac valve 18 will need to be determined. Various methods and devices for determining the dimensions of the annulus 18 of the cardiac valve 12 are known in the art, such as echocardiogram, computed tomography (CT), magnetic resonance imaging (MRI), fluoroscopy, and angiography. After determining the dimensions of the cardiac valve 18, an appropriately-sized first annuloplasty ring 14 having a suitably sized predetermined length 62 is chosen. The first annuloplasty ring 14 is suitably sized so that the dimensions of the distal end portion 56 of the first annuloplasty ring 14 correspond to the dimensions of the annulus 18 of the cardiac valve 12. For instance, a first annuloplasty ring 14 having a distal end portion 56 approximately equal to the circumference of the annulus 18 of the cardiac valve 12 may be selected.

Figure 7A:
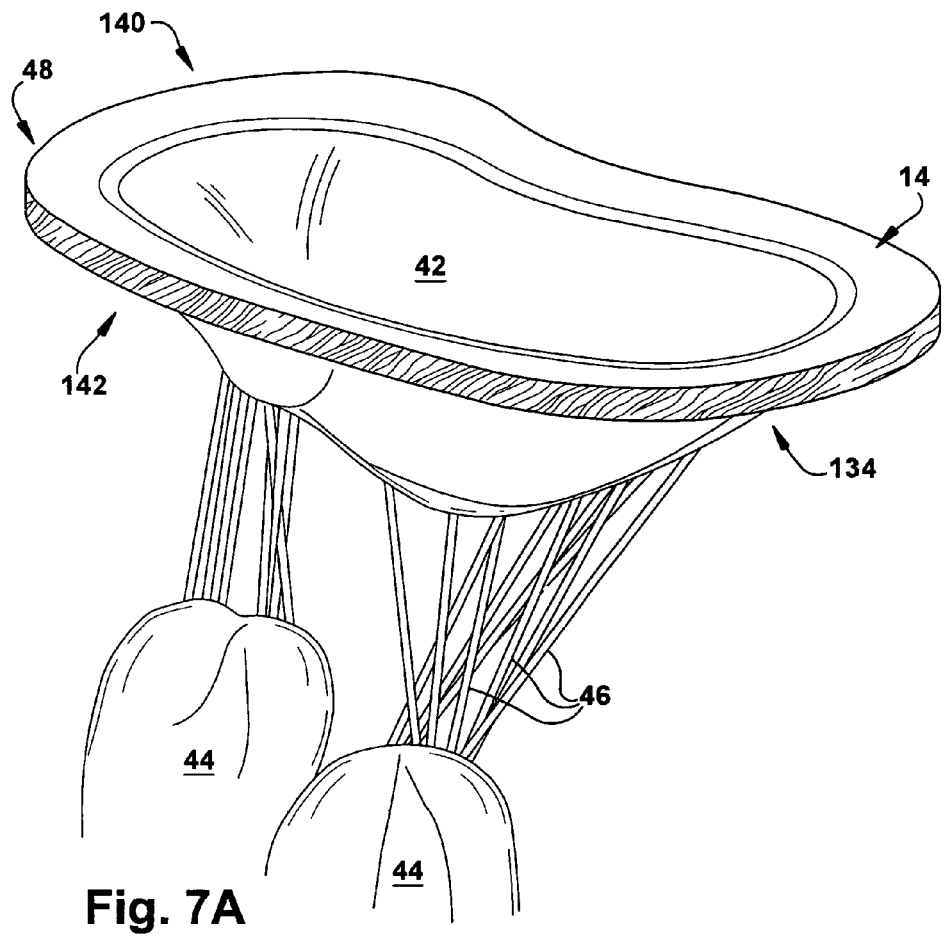
FIG. 7A is a perspective view of a regurgitant mitral valve.
Figure 7B:
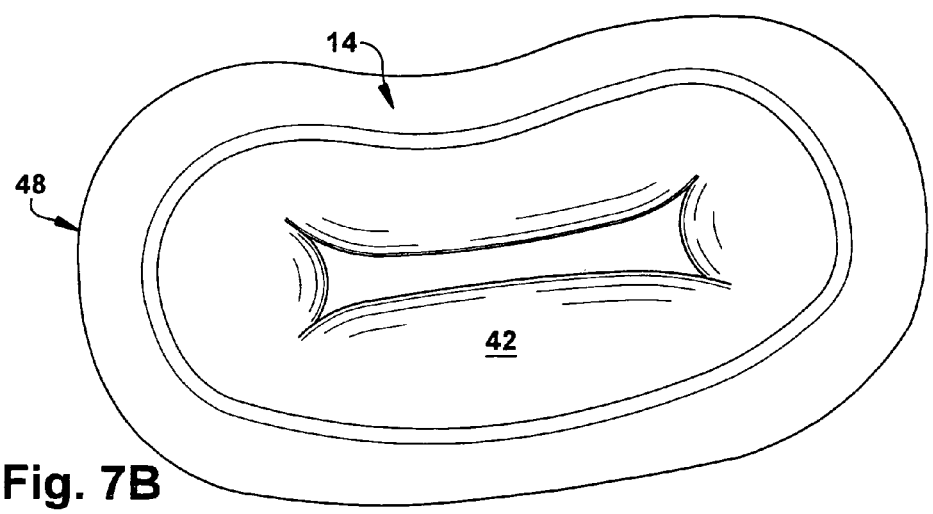
FIG. 7B is a plan view showing a superior aspect of the regurgitant mitral valve.

Next, the first annuloplasty ring 14 is inserted into the vasculature of a patient to repair, for example, a regurgitant mitral valve 42 (FIGS. 7A and 7B). Where an intravascular approach is desired, the first annuloplasty ring 14 may be inserted through a femoral artery or vein (not shown) via a delivery catheter 102. Alternatively, the first annuloplasty ring 14 may be inserted through the internal jugular vein (not shown). Further, the first annuloplasty ring 14 may be inserted using a transthoracic approach by introducing the first annuloplasty ring into the heart 20 via a minimally invasive incision or port on the heart wall.

Once the first annuloplasty ring 14 is inserted into the vasculature of the patient, the first annuloplasty ring is guided toward a first aspect of the cardiac valve annulus 138, such as a superior aspect 140 of the mitral valve annulus 48. The first annuloplasty ring 14 is inserted into an internal jugular vein (not shown), through the superior vena cava 30 into the right atrium 22, across the interatrial septum (not shown) to the left atrium 24, and then around the mitral annulus 48. Using tactile means, for example, the first annuloplasty ring 14 is guided toward the left atrium 24. It should be appreciated that other means may be used to guide the first annuloplasty ring 14. For instance, the first annuloplasty ring 14 may be guided toward the left atrium 24 using magnetic guidance, such as the Stereotaxis® Magnetic Navigation System, or robotic guidance to remotely control delivery of the first annuloplasty ring.

It should be appreciated that access to the superior aspect 140 of the mitral annulus 48 may also be gained via a femoral vein (not shown) by urging the first annuloplasty ring 14 through the inferior vena cava 32 into the right atrium 22, through the interatrial septum into the left atrium 24, and around the mitral annulus. Further, it should be appreciated that the first annuloplasty ring 14 may be delivered to an inferior aspect 142 of the mitral valve annulus 48, such as a subvalvular space (not shown in detail), roughly defined as the left ventricular side of the mitral annulus 48.

Figure 8A:
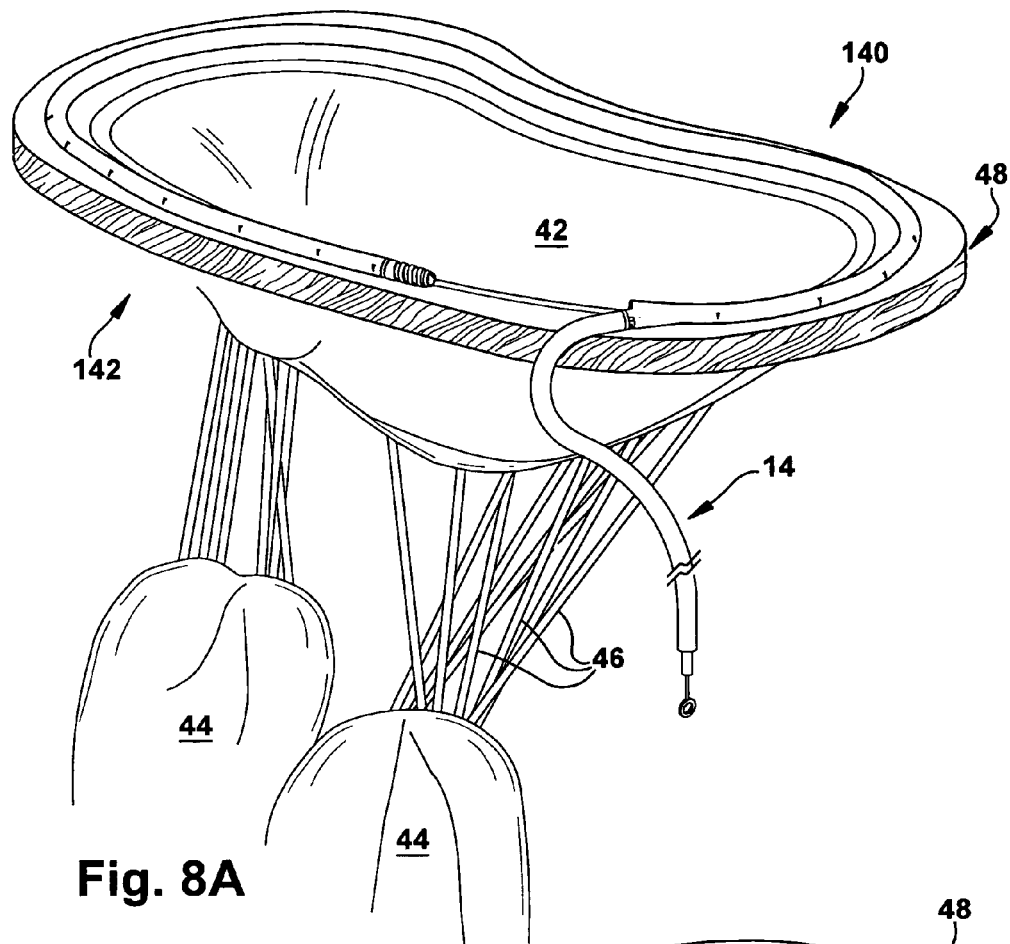
FIG. 8A is a perspective view showing the apparatus in FIG. 3 secured to the superior aspect of the regurgitant mitral valve.
Figure 8B:
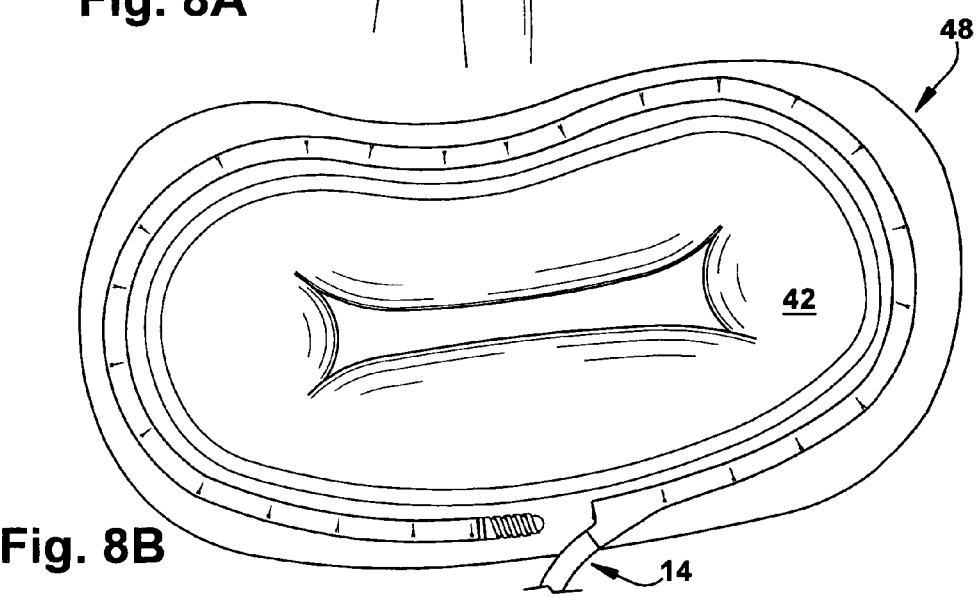
FIG. 8B is a plan view showing the apparatus in FIG. 8A secured to the superior aspect of the regurgitant mitral valve.

Once the first annuloplasty ring 14 has been suitably positioned at the first aspect 138 of the mitral annulus 48 (FIGS. 8A and 8B), the distal end portion 56 is attached to the mitral annulus by adjusting the deployable hook members 86 from a non-deployed configuration (FIGS. 9A and 9B) to a deployed configuration (FIG. 9C). The deployable hook members 86 may be deployed in a variety of ways. For instance, the deployable hook members 86 may be deployed via an electromagnetic mechanism (not show). The electromagnetic mechanism can comprise an electromagnetic wire (not show) operably linked to the deployable hook members 86. The electromagnetic wire can comprise the wire catheter 54 or, alternatively, an additional wire (not shown). The electromagnetic wire may also be operably linked to a battery or other power source capable of generating electricity. When electricity is supplied to the wire, the deployable hook members 86 change from the non-deployed configuration to the deployed configuration.

The deployable hook members 86 may also be deployed via a camming mechanism (not shown). The camming mechanism may comprise a tensioning wire (not shown)

operably linked to the deployable hook members 86. When the tensioning wire is manipulated, the deployable hook members 86 change from the non-deployed configuration to the deployed configuration. Alternatively, the deployable hook members 86 may be deployed as a result of the first annuloplasty ring 14 assuming a particular confirmation (e.g., by changing the first annuloplasty ring from a linear configuration to a circular or annular configuration). Also, an inflatable member (not shown) disposed within the first annuloplasty ring 14 may cause the deployable hook members 86 to deploy when inflated.

Figure 10:
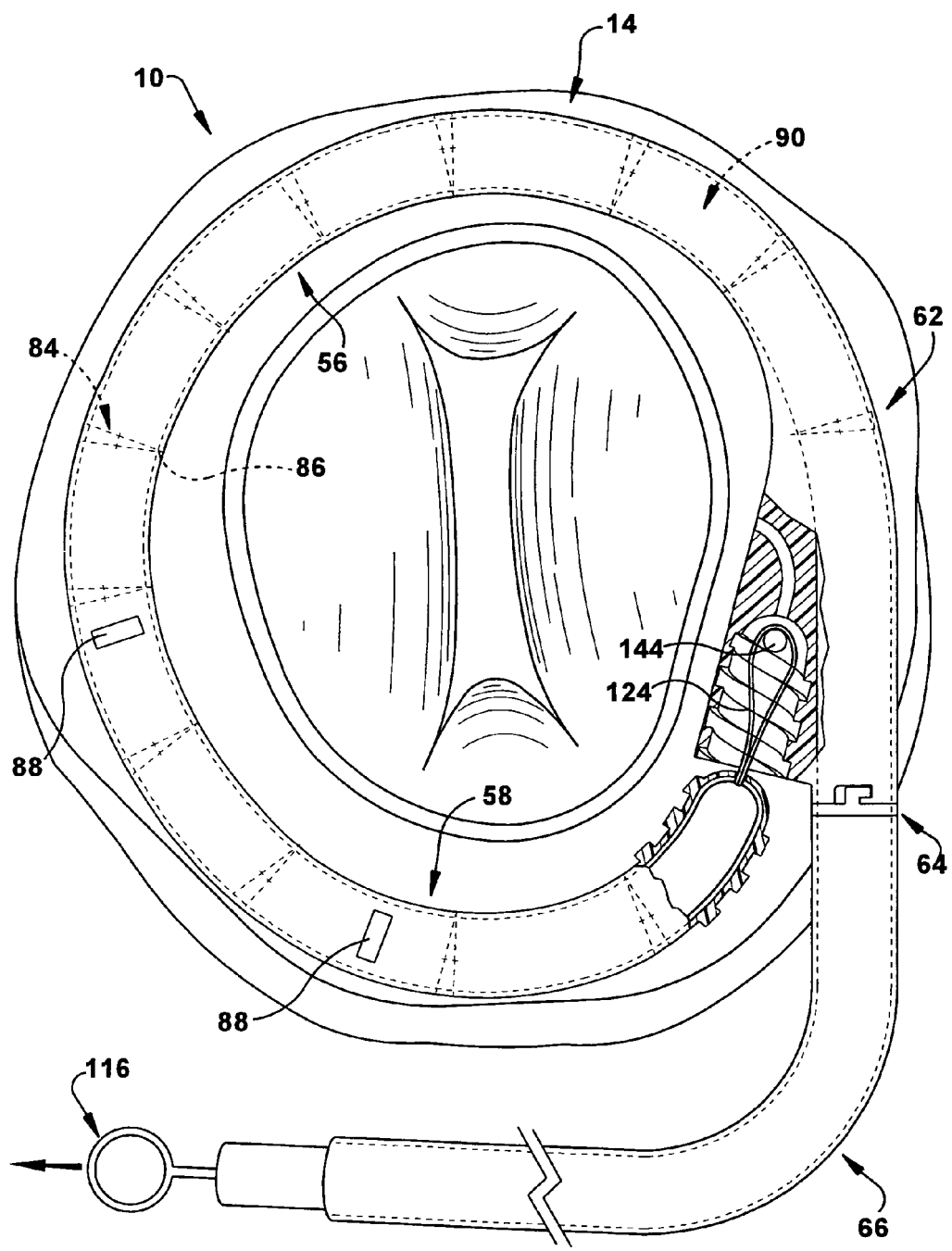
FIG. 10 is a perspective view showing the flexible body inserted in the apparatus shown in FIG. 3 in a deployed configuration.
Figure 12:
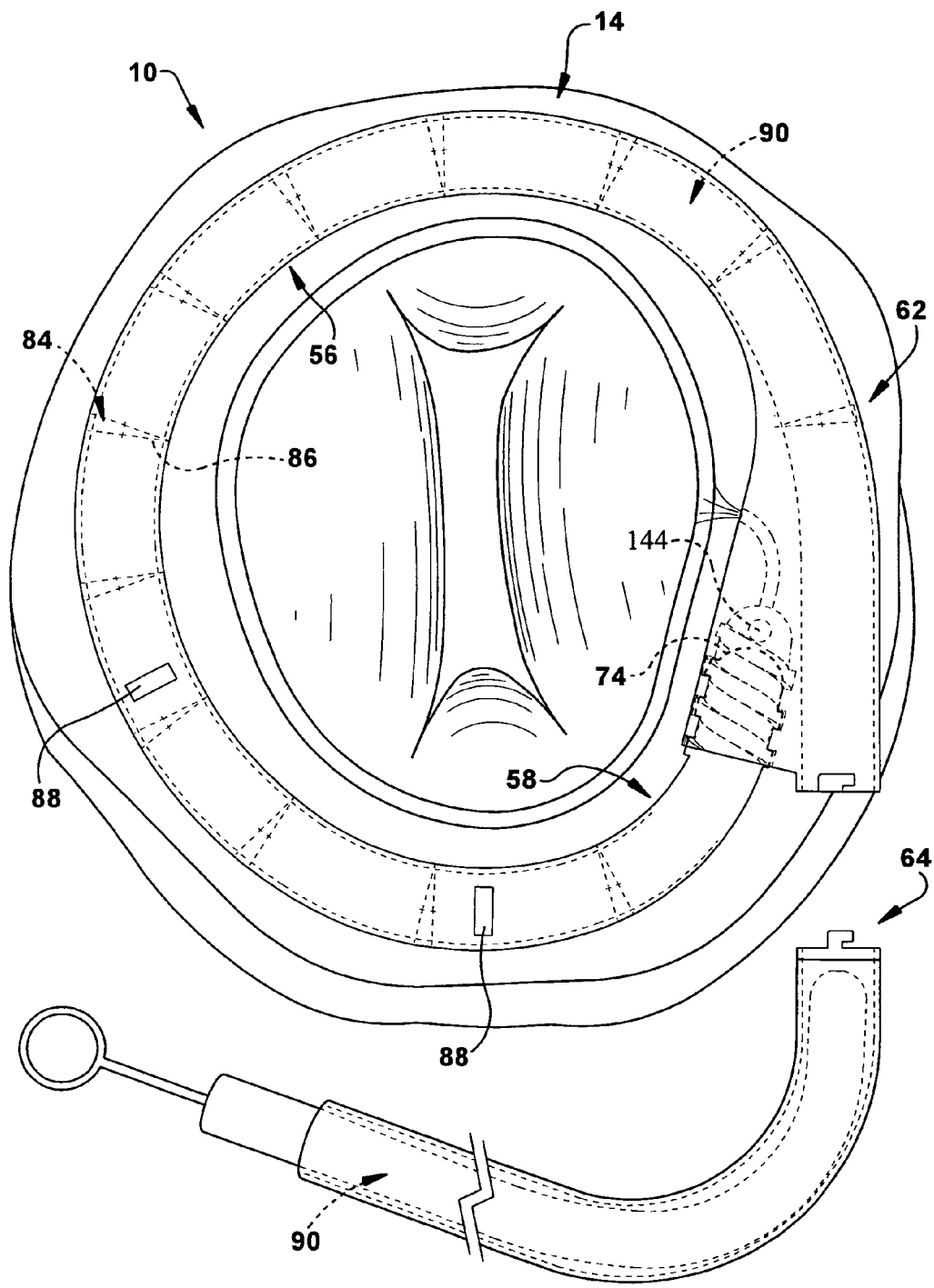
FIG. 12 is a perspective view showing the apparatus in FIG. 1 implanted on a normally functioning mitral valve.

After the distal end portion 56 of the first annuloplasty ring 14 is secured to the mitral annulus 48, the flexible body 90 is inserted into the main body portion 66 in a first relaxed configuration and then urged into the distal end portion of the first annuloplasty ring. When the distal end portion 94 of the flexible body 90 is positioned at the distal end portion 56, the terminal end 58 is then urged toward the connecting section 60 of the first annuloplasty ring 14. A radial force (indicated by the arrow) is next applied to the pull wire 116 of the flexible body 90 so that the loop member 124 extends through the opening 108 of the delivery catheter 102 and through the terminal end 58 of the first annuloplasty ring 14 (FIG. 10). As the loop member 124 is progressively exuded from the first annuloplasty ring 14, the distal end portion 94 obtains an open, lasso-like configuration as shown in FIG. 12. The position of the loop member 124 is then adjusted so that the loop member contacts a portion of the first annuloplasty ring 14.

As shown in FIG. 10, the loop member 124 is positioned so that the distal end portion 126 ensnares a portion of the first annuloplasty ring 14. More particularly, the loop member 124 is positioned so that the distal end portion 126 ensnares an anchor member 144 located in the receptacle portion 74 of the first annuloplasty ring 14. The anchor member 144 provides a means for connecting the distal end portion 126 of the loop member 124 with the first annuloplasty ring 14. In FIG. 10, for example, the anchor member 144 has a stub-like configuration; however, it will be appreciated that the anchor member may comprise any other form or shape capable of providing a secure point of contact with the harness member 114. By connecting the loop member 124 to the first annuloplasty ring 14, the diameter of the first annuloplasty ring may be modified (i.e., reduced) by withdrawing the pull wire 116. Although FIG. 10 depicts the anchor member 144 in the receptacle portion 74 of the first annuloplasty ring 14, it will be appreciated that the anchor member may be located anywhere on the first annuloplasty ring so long as the distal end portion 126 of the loop member 124 can contact the anchor member.

Figure 11:
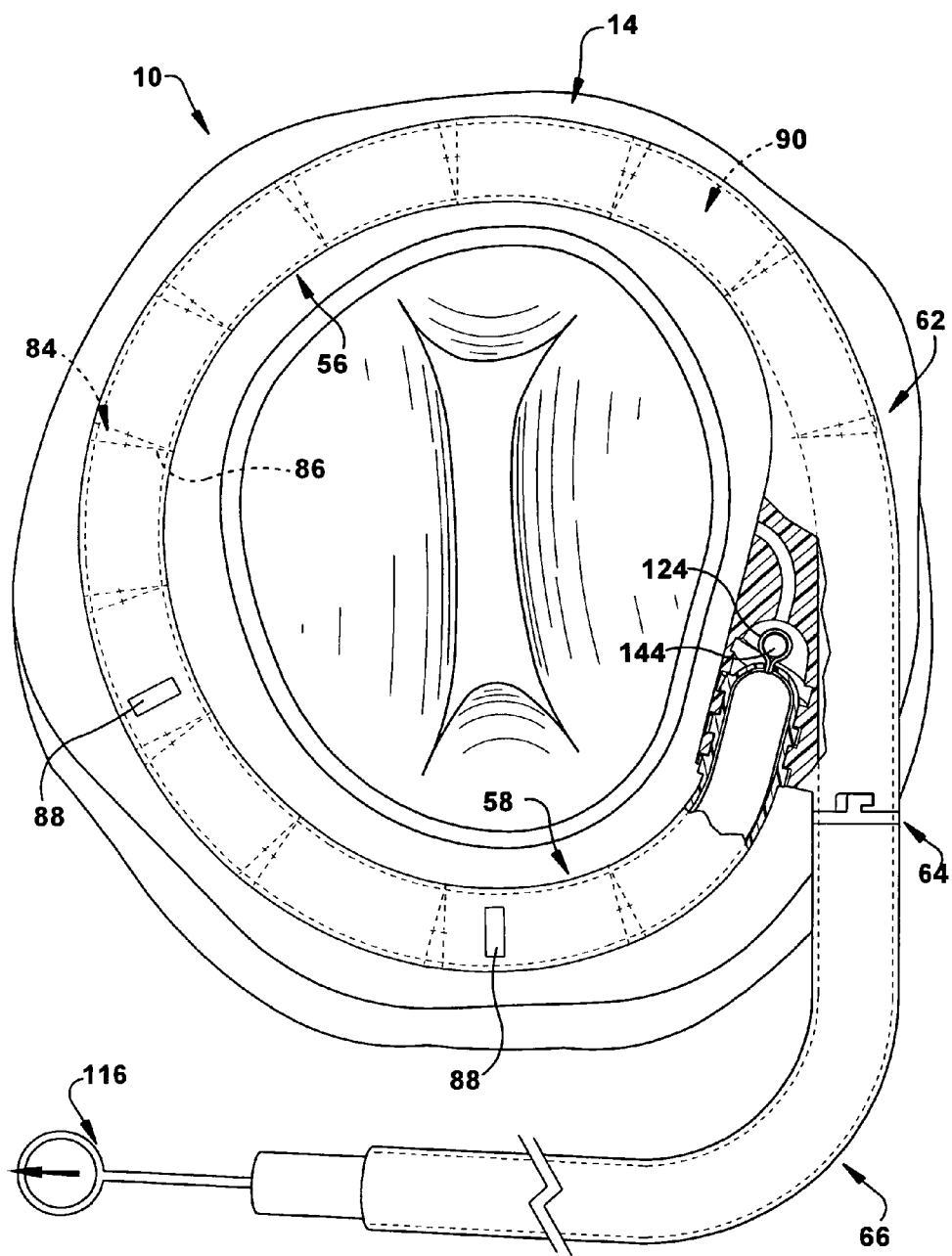
FIG. 11 is a perspective view showing the apparatus in FIG. 10 in a tensioned configuration.

As shown in FIG. 11, the pull wire 116 may then be withdrawn so that the distal end portion 126 of the loop member 124 is snugly cinched around the anchor member 144 and the terminal end 58 of the first annuloplasty ring 14 is pulled toward the receptacle portion 74. The terminal end 58 is securely interconnected to the connecting section 60 by manipulating the terminal end so that the threaded portion 78 is progressively threaded into the threaded portion 80 of the receptacle portion 74. As the terminal end 58 is progressively threaded into the receptacle portion 74, the diameter of the distal end portion 56 of the first annuloplasty ring 14 progressively shrinks so that the annulus 48 of the mitral valve 42 is remodeled. Once a complete ring 14 is formed, the diameter of the first annuloplasty ring may be adjusted by further withdrawing the pull wire 116. It is contemplated that the image guidance (e.g., MRI, CT, fluoroscopy, ultrasound, angiogram, or combinations thereof) may be used to monitor the degree to which the diameter of the distal end portion 56 is shrinking as the pull wire 116 is withdrawn.

The diameter of the first annuloplasty ring 14 may continue to be adjusted so that the leaflets of the mitral valve 42 properly coapt (FIG. 12) and regurgitation of blood flow through the mitral valve is reduced or eliminated. The distal end portion 126 of the loop member 124 is then loosened from the anchor member 144 and retracted into the delivery catheter 102. The flexible body 90 is withdrawn from the first annuloplasty ring 14 (FIG. 12), and the main body portion 66 is disconnected from the connecting section 60 by applying a force (e.g., torque) sufficient to separate the first and second ring members 68 and 70. After the connecting section 60 and the main body portion 66 are disconnected, the main body portion is retracted and the medical procedure completed. With the distal end portion 56 of the first annuloplasty ring 14 now securely attached to the mitral annulus 48, the mitral valve 42 is successfully remodeled and the patient is provided with a normally functioning mitral valve.

It should be appreciated that the method described above may be varied as needed. In one variation, for example, a first annuloplasty ring 14 may be sized and then percutaneously delivered to a superior aspect 140 of the mitral valve annulus 48 (as described above). After the first annuloplasty ring 14 is appropriately positioned about the mitral annulus 48, the flexible body 90 may then be inserted into the first annuloplasty ring and threaded into the distal end portion 56 of the first annuloplasty ring (as described above).

When the distal end portion 94 of the flexible body 90 is appropriately positioned at the distal end portion 56 of the first annuloplasty ring 14, the terminal end 58 may be urged toward the connecting section 60. A radial force may then be applied to the pull wire 116 so that the loop member 124 extends through the opening 108 of the delivery catheter 102 and through the terminal end 58 of the first annuloplasty ring 14. Either simultaneous with or shortly after extending the loop member 124, the deployable hook members 86 may then be deployed as described above to secure the distal end portion 56 of the first annuloplasty ring 14 to the mitral annulus 48. As described above, the distal end portion 126 of the loop member 124 may then be contacted with an anchor member 144 and appropriately adjusted to form a completed first annuloplasty ring 14. The flexible body 90 and the first annuloplasty ring 14 may then be adjusted further so that regurgitation of blood flow through the mitral valve 42 is reduced or eliminated. The flexible body 90 and the main body portion 66 of the first annuloplasty ring 14 may then be removed from the patient and the procedure completed (as described above).

In another variation of the method, a first annuloplasty ring 14 may be sized and percutaneously delivered a superior aspect 140 of the mitral valve annulus 48 as described above. Once the first annuloplasty ring 14 has been suitably positioned in the left atrium 24, the terminal end 58 of the first annuloplasty ring may be guided toward the connecting section 60. When the terminal end 58 is positioned adjacent the connecting section 60, the second magnet 82 of the terminal end may be magnetically attracted to the first magnet 76 of receptacle portion 74 so that the terminal end and the connecting section are magnetically held in contact. Consequently, the distal end portion 56 of the first annuloplasty ring 14 may be formed into a circular or annular shape. The distal end portion 56 may then be positioned adjacent the superior aspect 140 of the mitral annulus 48 and secured thereto by deploying the deployable hook members 86 as described above.

Next, the terminal end 58 of the first annuloplasty ring 14 may be securely interconnected with the connecting section 60 to form a ring (as described above). After the first annuloplasty ring 14 is securely positioned about the mitral annulus 48, the flexible body 90 may be inserted into the first annuloplasty ring as described above. The cinching mechanism 100 of the flexible body 90 may then be operated as described above to adjust (i.e., reduce) the diameter of the distal end portion 56 of the first annuloplasty ring 14 and modify the mitral annulus 48 so that the mitral leaflets properly coapt and regurgitation of blood flow through the mitral valve 42 is reduced or eliminated. The flexible body 90 and main body portion 66 of the first annuloplasty ring 14 may then be removed and the medical procedure completed (as described above).

An alternate embodiment of the method comprises using a flexible body 90, a first annuloplasty ring 14, and a second annuloplasty ring 134 to remodel the annulus 18 of a cardiac valve 12 to reduce regurgitation of blood flow through the cardiac valve. As described above, the second annuloplasty ring 134 can comprise any type of annuloplasty ring known in the art and described above. Alternatively, the second annuloplasty ring 134 may be identically constructed as the first annuloplasty ring 14. Where the second annuloplasty ring 134 is identically constructed as the first annuloplasty ring 14, the second annuloplasty ring may first be sized to a second aspect 136 of the mitral annulus 48, such as an inferior aspect 142 of the mitral valve annulus 48, in a manner similar to the first annuloplasty ring 14 (described above).

The first annuloplasty ring 14 may then be inserted into the vasculature of a patient as described above and urged toward the first aspect 138 of the mitral valve 42. After inserting the first annuloplasty ring 14, the second annuloplasty ring 134 may be inserted into the vasculature of the patient. For instance, the second annuloplasty ring 134 may be inserted into a femoral artery (not shown), across the aortic arch 146, through the aortic valve 38, and into the left ventricle 28. After delivering the first and second annuloplasty rings 14 and 134 to the superior and inferior aspects 140 and 142 of the mitral annulus 48, respectively, the deployable hook members 86 of each of the first and second annuloplasty rings may be deployed (as described above) to respectively secure the first and second annuloplasty rings to the superior and inferior aspects of the mitral valve. At least one magnetic element 88 of the first annuloplasty ring may be magnetically attracted to at least one magnetic element of the second annuloplasty ring 134 so that the first and second annuloplasty rings are magnetically coupled together and the mitral annulus 48 is fit between the first and second annuloplasty rings.

Next, the terminal end 58 of the second annuloplasty ring 134 is guided toward the connecting section 60 of the second annuloplasty ring. When the terminal end 58 of the second annuloplasty ring 134 is positioned adjacent the connecting section 60, the second magnet 82 of the terminal end is magnetically attracted to the first magnet 76 of the receptacle portion 74 so that the distal end portion 56 of the second annuloplasty ring is magnetically held in contact with the connecting section of the second annuloplasty ring.

The terminal end 58 of the second annuloplasty ring 134 may then be interconnected with the connecting section 60 to form a continuous ring. The terminal end 58 of the second annuloplasty ring 134 may be securely interconnected to the connecting section 60 by manipulating the terminal end so that the threaded portion 78 of the second annuloplasty ring is progressively threaded into the threaded portion 80. As the terminal end 58 of the second annuloplasty ring 134 is progressively threaded into the receptacle portion 74, the distal end portion 56 of the second annuloplasty ring 134 may be securely attached to the second aspect 136 of the mitral annulus 48. After the distal end portion 56 of the second annuloplasty ring 134 is secured about the inferior aspect 142 of the mitral annulus 48, the connecting section 60 of the second annuloplasty ring may be disconnected from the main body portion 66 and the main body portion retracted from the vasculature of the patient.

With the second annuloplasty ring 134 secured about the inferior aspect 142 of the mitral valve annulus 48, the flexible body 90 may be inserted into the first annuloplasty ring 14 and advanced to the distal end portion 56 of the first annuloplasty ring, as described above. The cinching mechanism 100 of the flexible body 90 may then be adjusted so that the flexible body obtains the second tensioned configuration, thereby causing the first annuloplasty ring 14 to modify the mitral annulus 48 so that the mitral leaflets properly coapt. The flexible body 90 and the main body portion 66 of the first annuloplasty ring 14 may then be retracted from the vasculature of the patient as described above. With the distal end portion 56 of each of the first and second annuloplasty rings 14 and 134 respectively secured to the superior and inferior aspects 140 and 142 of the mitral valve annulus 48 as shown in FIGS. 6A and 6B, the mitral annulus 48 is remodeled to reduce or eliminate regurgitation of blood flow through the mitral valve.

Another embodiment of the present invention is illustrated in FIGS. 13-24. The apparatus 10a is identically constructed as the apparatus 10 shown in FIG. 1, except where as described below. In FIG. 13-24, structures that are identical as structures in FIG. 1 use the same reference numbers, whereas structures that are similar but not identical carry the suffix "a".

Figure 13:
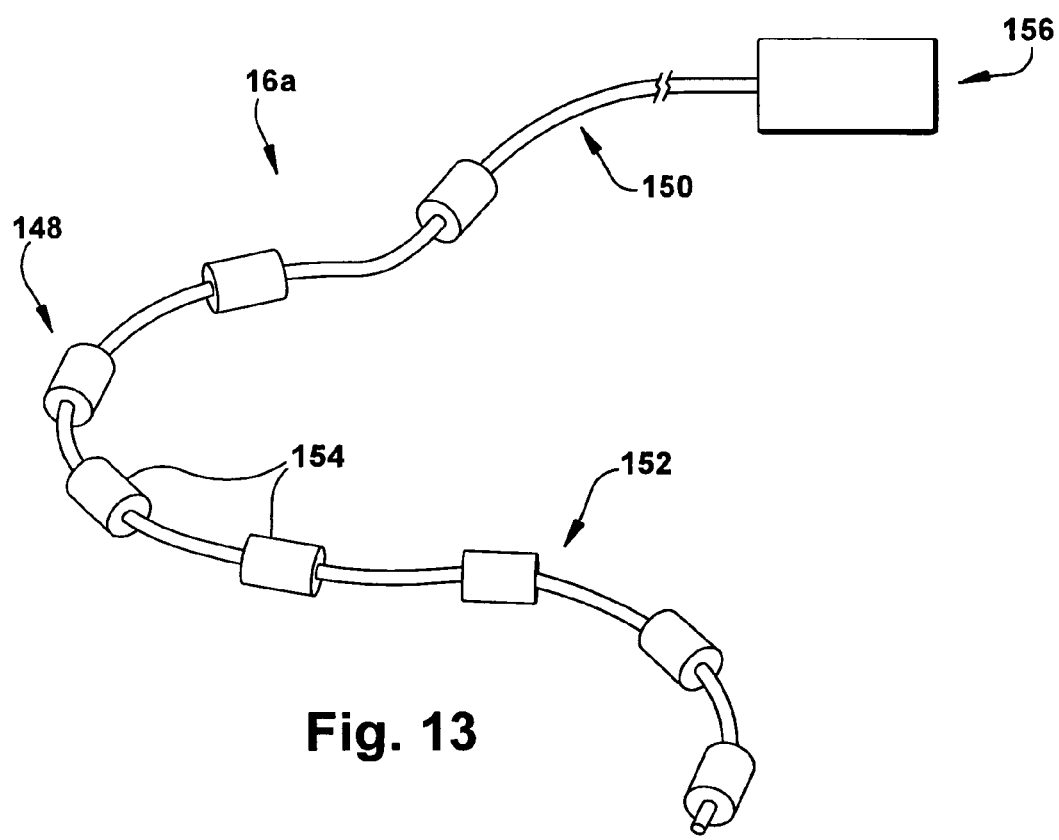
FIG. 13 is a perspective view showing another alternative embodiment of the apparatus shown in FIG. 1 comprising an electromagnetic wire.

An apparatus $10_a$ for modifying the annulus 18 of a cardiac valve 14 to reduce regurgitation of blood flow through the cardiac valve comprises a first annuloplasty ring 14 (FIG. 3) and an elongate flexible body $16_a$ (FIG. 13). The elongate flexible body 166a comprises an electromagnetic wire 148 having proximal and distal end portions 150 and 152. It should be appreciated that the term "wire" as used herein is a broad term having its normal and customary meaning and includes, without limitation, mesh, flat, round, band-shaped, and rod-shaped members. The electromagnetic wire 148 includes a plurality of magnetic members 154 operably connected to the electromagnetic wire, and an adjustable mechanism (not shown in detail) for adjusting the electromagnetic wire from a first relaxed configuration to a second tensioned configuration.

The electromagnetic wire 148 and the magnetic members 154 are comprised of a ferromagnetic material. The term "ferromagnetic" as used herein is a broad term and is used in its ordinary sense and includes, without limitation, any material that easily magnetizes, such as a material having atoms that orient their electron spins to conform to an external magnetic field. Ferromagnetic materials include a variety of permanent magnets, which can be magnetized through a variety of modes, and materials, such as metals, that are attracted to permanent magnets. Ferromagnetic materials are capable of being activated by an electromagnetic transmitter, such as one located outside of a patient.

Ferromagnetic materials can include at least one of Fe—C, Fe—Pd, Fe—Mn—Si, Co—Mn, Fe—Co—Ni—Ti, Ni—Mn—Ga, $Ni_2MnGa$, and Co—Ni—Al. Ferromagnetic materials may also include one or more polymer-bonded magnets, wherein magnetic particles are bound within a polymer matrix, such as a biocompatible polymer. Ferromagnetic materials of the present invention can additionally comprise isotropic and/or anisotropic materials, such as for example NdFeB, SmCo, ferrite and/or AlNiCo particles. The biocompatible polymer can comprise, for example, polycarbonate, silicone rubber, polyurethane, silicone elastomer, a flexible or semi-rigid plastic, combinations of the same and the like.

Figure 14A:
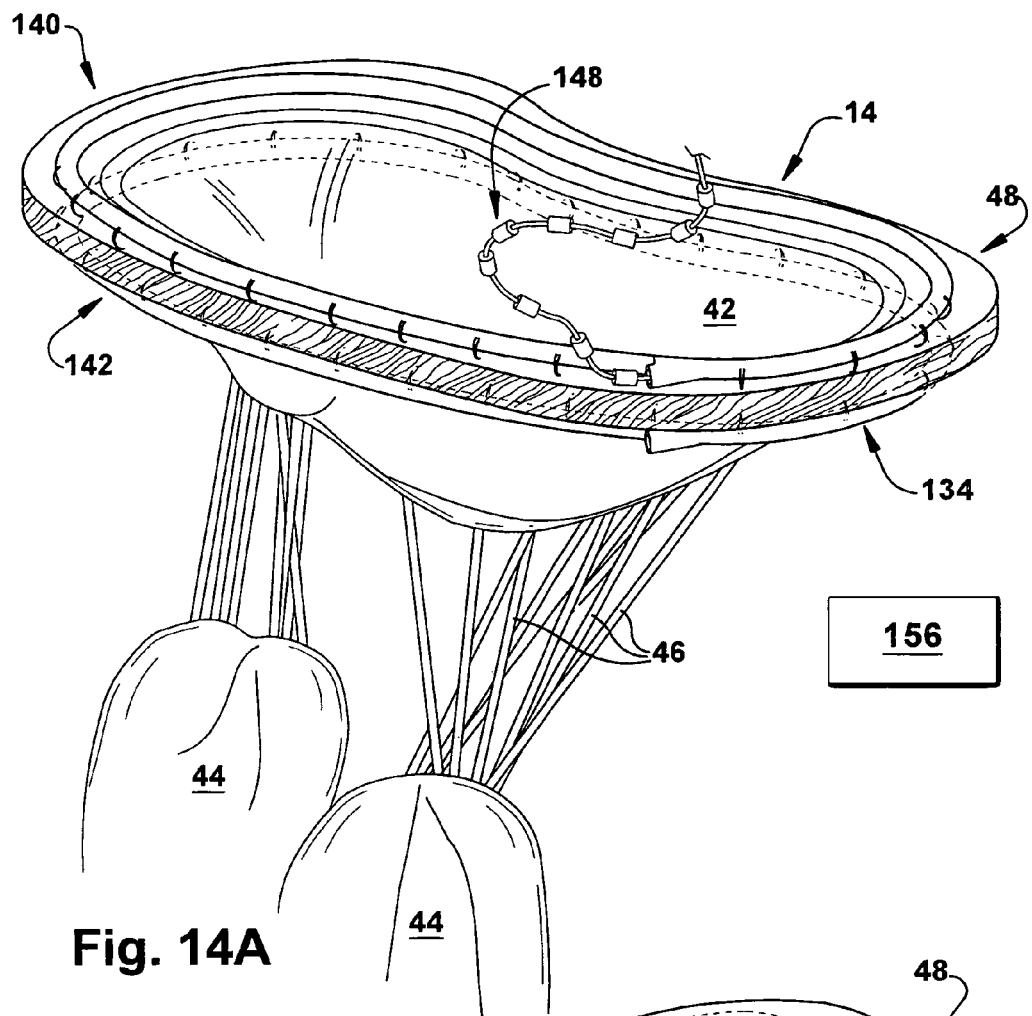
FIG. 14A is a perspective view of an alternate embodiment of the apparatus shown in FIG. 13 implanted on a superior aspect of a regurgitant mitral valve showing the electromagnetic wire being inserted into the first annuloplasty ring.
Figure 14B:
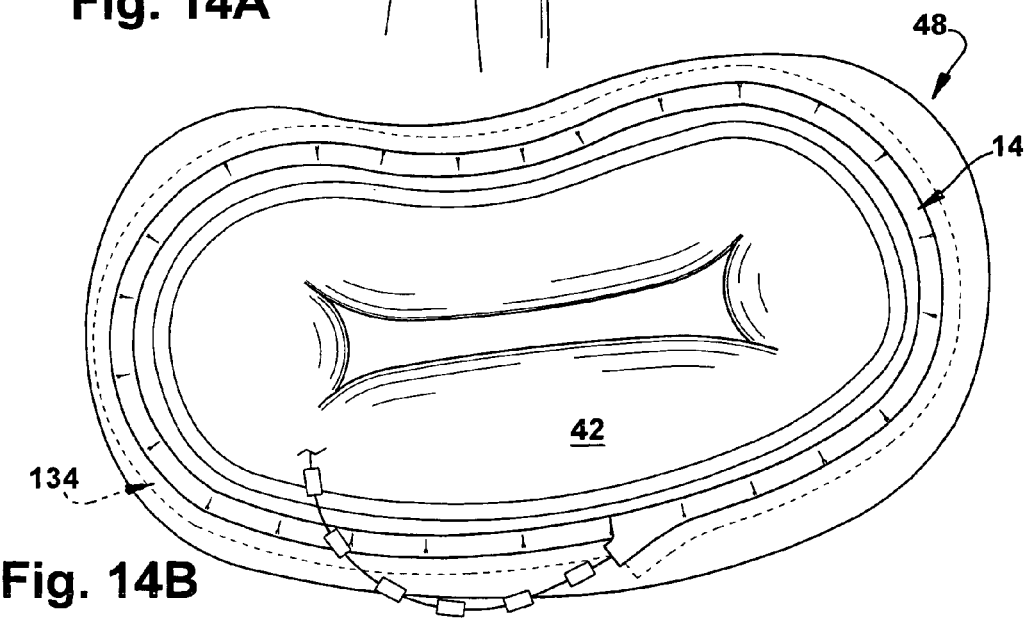
FIG. 14B is a plan view showing the apparatus of FIG. 14A implanted on the superior aspect of the regurgitant mitral valve.

As shown in FIG. 13, an external energy source 156 for delivering electromagnetic energy to the electromagnetic wire 148 may be operably coupled to the proximal end portion 150 of the electromagnetic wire. Alternatively, the external energy source 156 may be wirelessly coupled to the electromagnetic wire 148 (FIGS. 14A and 14B). The energy source 156 may include, for example, radio frequency (RF) energy, X-ray energy, microwave energy, acoustic or ultrasound energy such as focused ultrasound or high intensity focused ultrasound energy, light energy, electric field energy, laser energy, magnetic field energy, combinations of the same, or the like.

The magnetic members 154 (FIG. 13) facilitate modification of the electromagnetic wire 148 from the first relaxed configuration to the second tensioned configuration. In the first relaxed configuration, for example, electromagnetic energy is not applied to the electromagnetic wire 148 and the electromagnetic wire obtains a pliable or flexible configuration. The first relaxed configuration facilitates placement of the electromagnetic wire 148 into the first annuloplasty ring 14. When electromagnetic energy is delivered to the electromagnetic wire 148, each of the magnetic members 154 is magnetically polarized. Opposing magnetic poles of adjacent magnetic members 154 are then attracted to one another. The magnetic force between the magnetic members 154 causes the magnetic members to gravitate towards one another and the electromagnetic wire 148 to shrink and obtain the second tensioned configuration. The number and shapes selected for the magnetic members 154 may depend, at least in part, on factors such as the desired field to be produced, the resulting mutual force or forces between the magnetic members, or the like.

As discussed in greater detail below, the electromagnetic wire 148 may be inserted into the first annuloplasty ring 14 in the first relaxed configuration and then magnetized by the external energy source 156 so that the electromagnetic wire obtains the second tensioned configuration. When the electromagnetic wire 148 obtains the second tensioned configuration, the diameter of the first annuloplasty ring 148 may be uniformly modified, i.e., reduced in 360°. Alternatively, by selectively depositing an insulative material (e.g., a rubber or plastic polymer) on the electromagnetic wire 148, only select portions of the first annuloplasty ring, such as portions spaced approximately 180° apart, may be reduced when electromagnetic energy is applied to the electromagnetic wire.

Another embodiment of the present invention comprises an electromagnetic wire 148, a first annuloplasty ring 14, and a second annuloplasty ring 134 (FIGS. 14A and 14B). As described above, the second annuloplasty ring 134 may be disposed about a second aspect 136 of a cardiac valve 12, such as an inferior aspect 142 of the mitral valve annulus 48 (FIGS. 15A and 15B), and may comprise any type of annuloplasty ring known in the art. The second annuloplasty ring 134 may facilitate placement of the first annuloplasty ring 14 about a superior aspect 140 of the mitral valve annulus 48, for example.

In another embodiment of the present invention, the apparatus $10_a$ may be percutaneously delivered to modify the annulus 18 of a cardiac valve 12 to reduce regurgitation of blood flow through the cardiac valve. For example, the apparatus $10_a$ can be percutaneously delivered to a first aspect 138 of a cardiac valve 12, such as a superior aspect 140 of the mitral valve annulus 48, to reduce or eliminate regurgitation of blood flow through the mitral valve.

Figure 18:
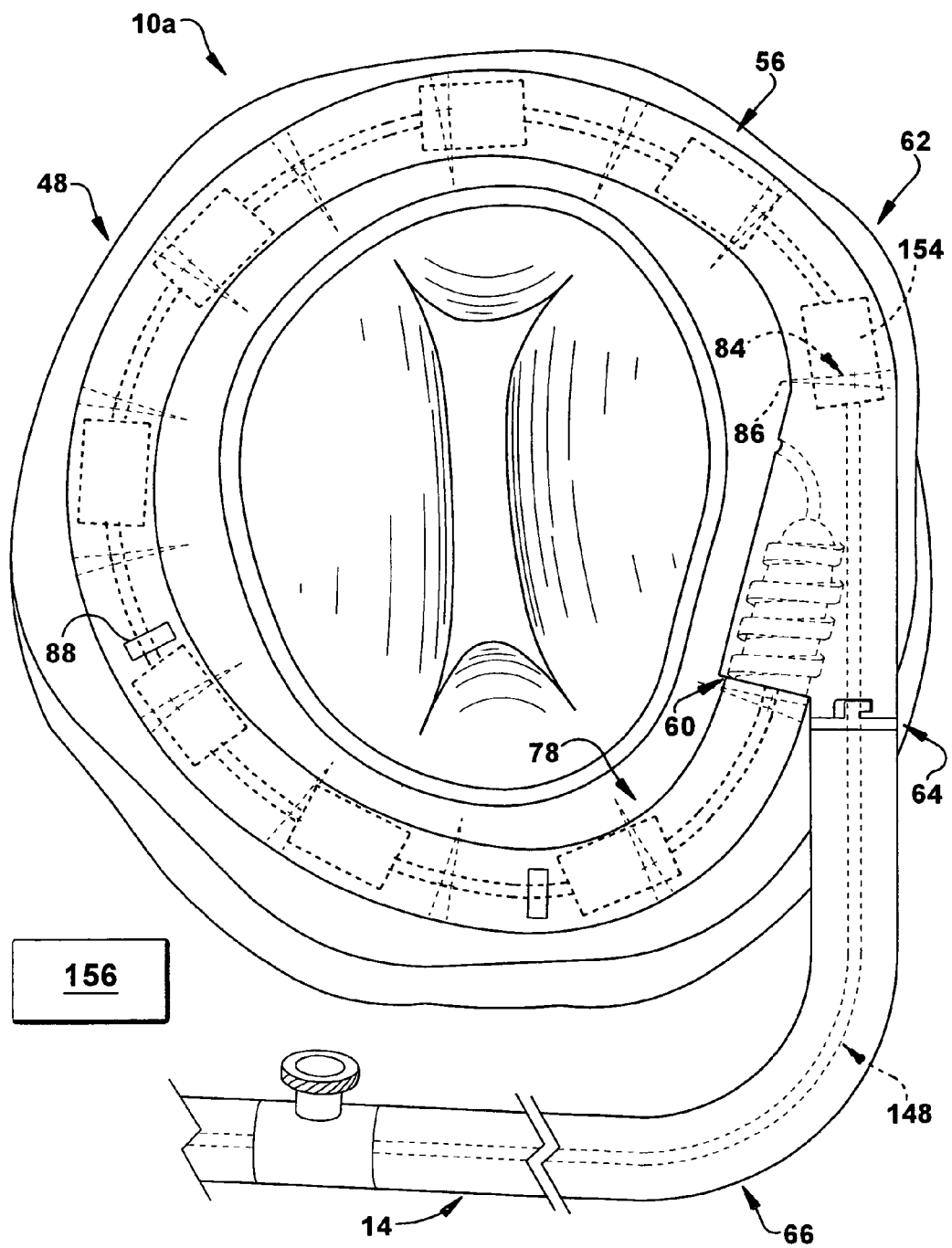
FIG. 18 is a perspective view showing the apparatus of FIG. 13 secured to the superior aspect of the regurgitant mitral valve annulus and inserted into the first annuloplasty ring.
Figure 19:
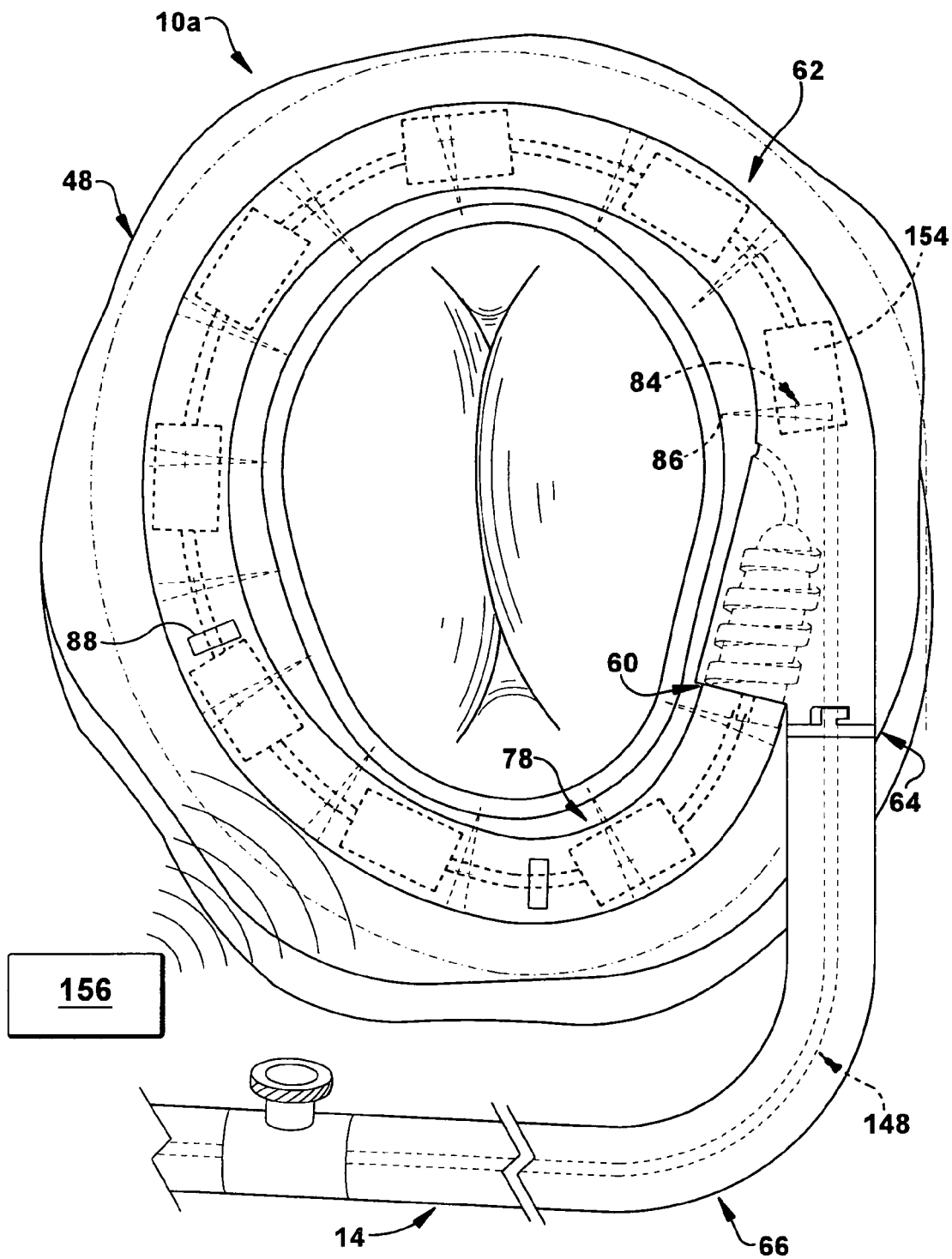
FIG. 19 is a perspective view showing the apparatus of FIG. 18 secured to the superior aspect of the regurgitant mitral valve annulus and changing from a first relaxed configuration (dotted lines) to a second tensioned configuration (solid lines)

The mitral annulus 48 and the first annuloplasty ring 14 may be sized as described above. Next, the first annuloplasty ring 14 may be delivered to the left atrium 24 and securely positioned about the mitral annulus 48 (FIGS. 16 and 17) as described above. An electromagnetic wire 148 having a first relaxed configuration may then be inserted into the main body portion 66 and urged into the distal end portion 56 of the first annuloplasty ring 14 (FIG. 18).

Figure 21:
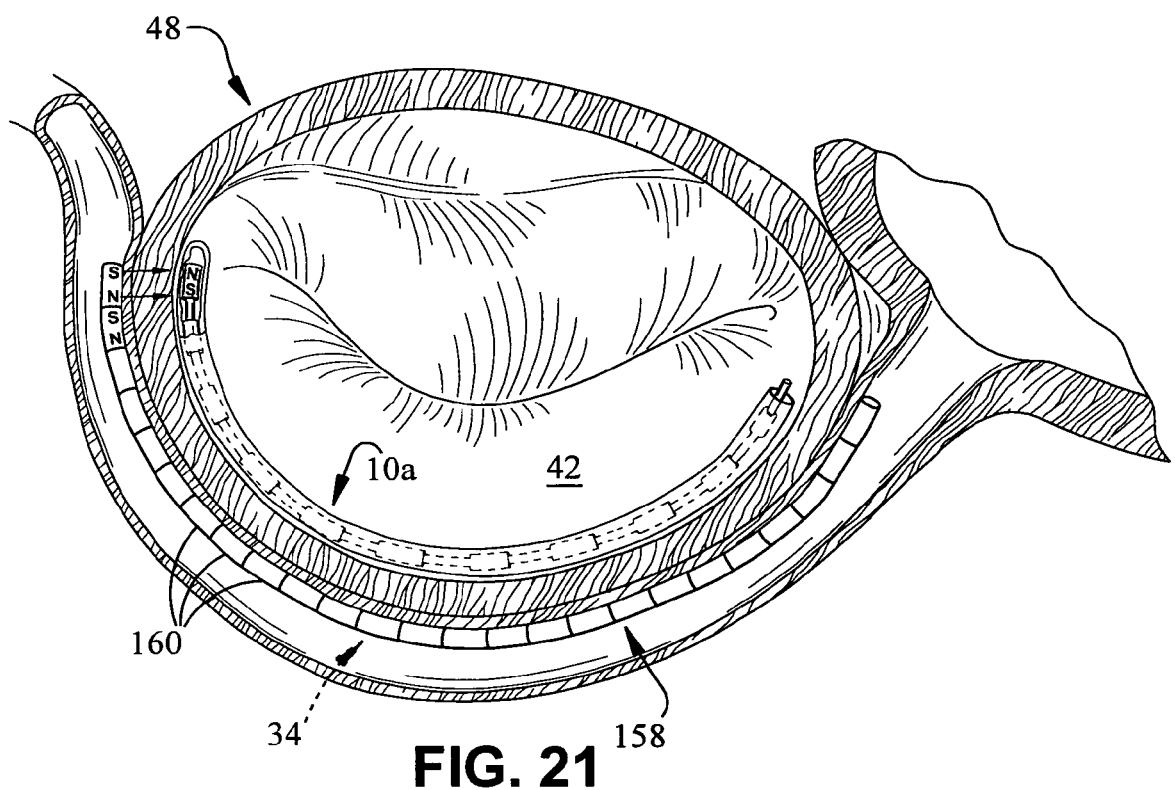
FIG. 21 is a plan view showing the positioning catheter of FIG. 20 positioned across a left atrial wall from the apparatus shown in FIG. 22.
Figure 22:
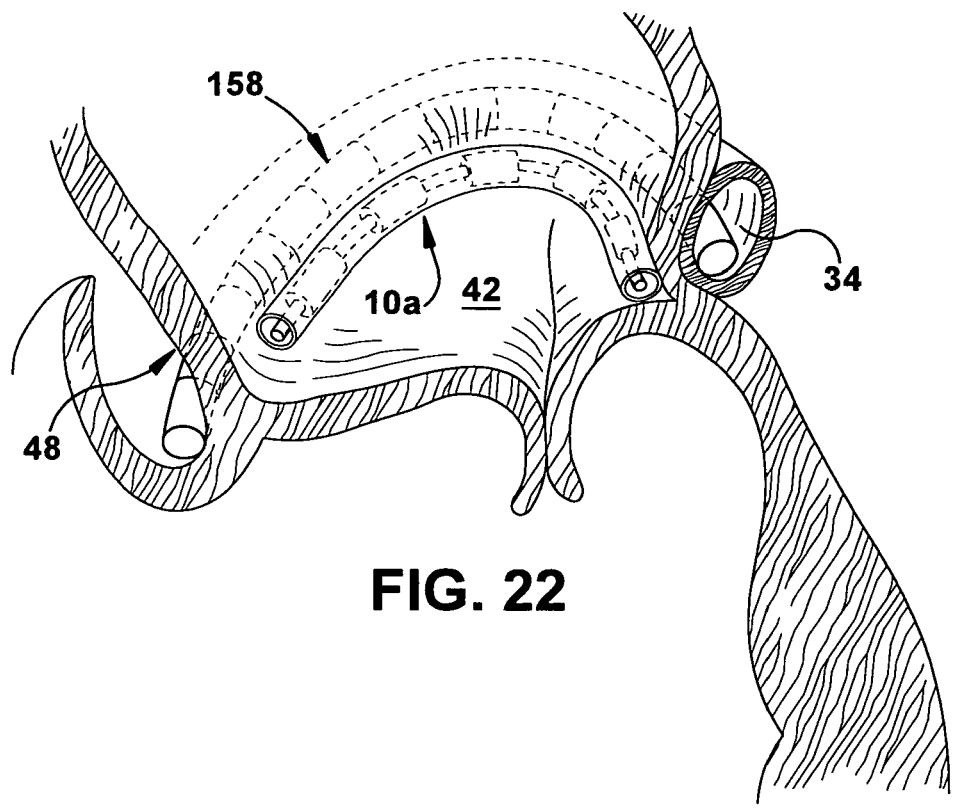
FIG. 22 is a magnified cross-sectional view of FIG. 21.

Once the distal end portion 152 of the electromagnetic wire 148 is appropriately positioned in the first annuloplasty ring 14, electromagnetic energy (e.g., RF energy) may be delivered to the electromagnetic wire (FIG. 19) via the external energy source 156. As shown in FIG. 20, a positioning catheter 158 may be used to facilitate placement of the first annuloplasty ring 14 about the mitral annulus 48. The positioning catheter 158 can comprise a plurality of discrete magnets 160 disposed within a delivery sheath 162. The positioning catheter 158 may be inserted into the vasculature of the patient and then advanced into the coronary sinus 34 approximately adjacent the mitral annulus 48 (FIG. 21). As the first annuloplasty ring 14 is being aligned and placed near the mitral annulus 48, the magnet element(s) 88 of the first annuloplasty ring may be magnetically attracted to the positioning catheter 158 across the atrial wall (FIG. 22). The position of the positioning catheter 158 may then be further adjusted to place the first annuloplasty ring 14 as desired.

Once the electromagnetic wire 148 is appropriately positioned, the electromagnetic wire may be magnetized by delivering electromagnetic energy to the electromagnetic wire. Delivery of electromagnetic energy magnetizes the magnetic members 154 and causes the magnetic members to be magnetically attracted to one another. The magnetic attraction then causes the magnetic members 154 to gravitate towards one another, thereby causing the electromagnetic wire 148 to shrink and obtain the second tensioned configuration. Consequently, the first diameter (as shown by the dashed lines in FIG. 19) of the first annuloplasty ring 14 is reduced and the annulus 48 of the mitral valve 42 is modified so that the mitral leaflets properly coapt and regurgitation of blood flow through the mitral valve is reduced or eliminated.

Figure 24:
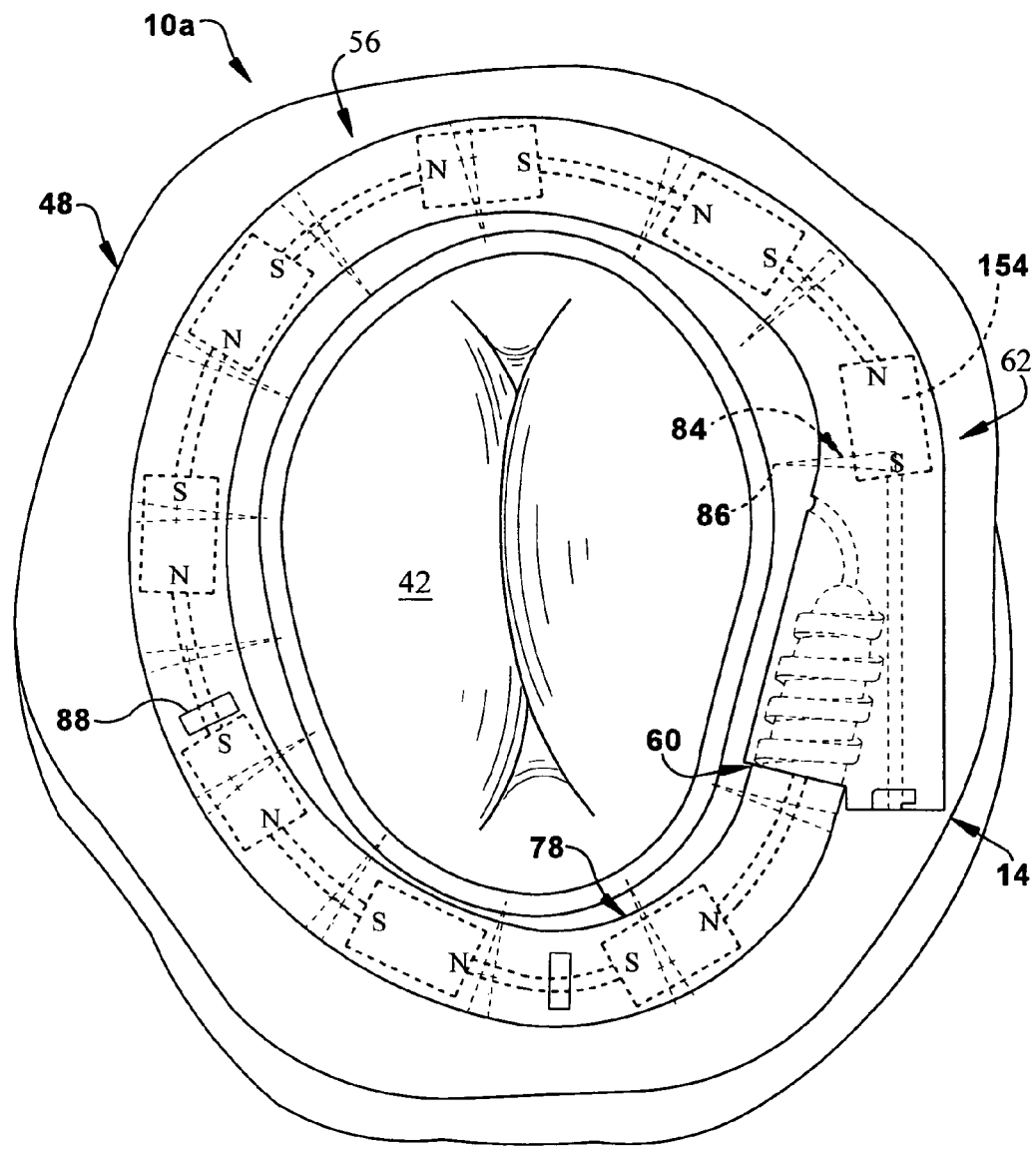
FIG. 24 is a perspective view of the apparatus in FIG. 19 showing the remodeled mitral valve and normal coaptation of the mitral valve leaflets.

After the first annuloplasty ring 14 is properly adjusted, the proximal end portion 150 of the electromagnetic wire 148 may be disconnected from the distal end portion 152 and removed from the vasculature of the patient (FIG. 24). The main body portion 66 may also be disconnected from the distal end portion 56 of the first annuloplasty ring 14 as described above. It should be appreciated that the method for percutaneously modifying a cardiac valve 12 using the apparatus $10_a$ is not limited to the sequence described above and, rather, that any combination of the above-described steps may be used to reduce regurgitation of blood flow through the cardiac valve.

Referring to FIGS. 14A and 14B, an alternate embodiment of the method comprises using first and second annuloplasty rings 14 and 134 to reduce regurgitation of blood flow through a cardiac valve 12. For example, first and second annuloplasty rings 14 and 134 may be respectively delivered to the superior and inferior aspects 140 and 142 of the mitral valve annulus 48 to reduce or eliminate mitral regurgitation. The second annuloplasty ring 134 may be identically constructed as the first annuloplasty ring 14. As described above, both the first and second annuloplasty rings 14 and 134 may then be delivered to the superior and inferior aspects 140 and 142 of the mitral valve annulus 48, respectively, as shown in FIGS. 14A and 14B.

Figure 23:
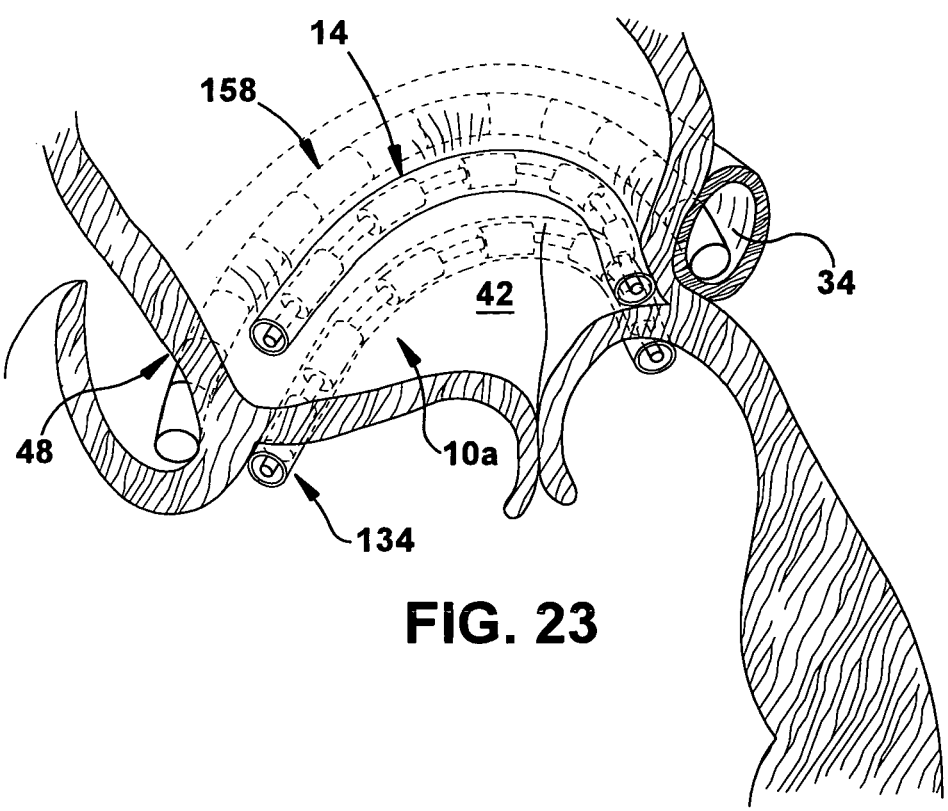
FIG. 23 is a magnified cross-sectional view similar to FIG. 21 showing an alternate embodiment of the present invention.

As shown in FIG. 23, a positioning catheter 158 may be used to facilitate placement of the first and second annuloplasty rings 14 and 134 about the superior and inferior aspects 140 and 142 of the mitral annulus 48 (respectively). As described above, the positioning catheter 158 can comprise a plurality of discrete magnets 160 disposed within a delivery sheath 162. The positioning catheter 158 may be inserted into the vasculature of the patient and then advanced into the coronary sinus 34 approximately adjacent the mitral annulus 48. As the first and second annuloplasty rings 14 and 134 are being aligned and placed near the superior and inferior aspects 140 and 142 of the mitral annulus 48 (respectively), the magnet element(s) 88 of the first and second annuloplasty rings may be magnetically attracted to the positioning catheter 158 across the atrial wall (FIG. 23). The position of the positioning catheter 158 may then be further adjusted to place the first and second annuloplasty rings 14 and 134 as desired.

Figure 15A:
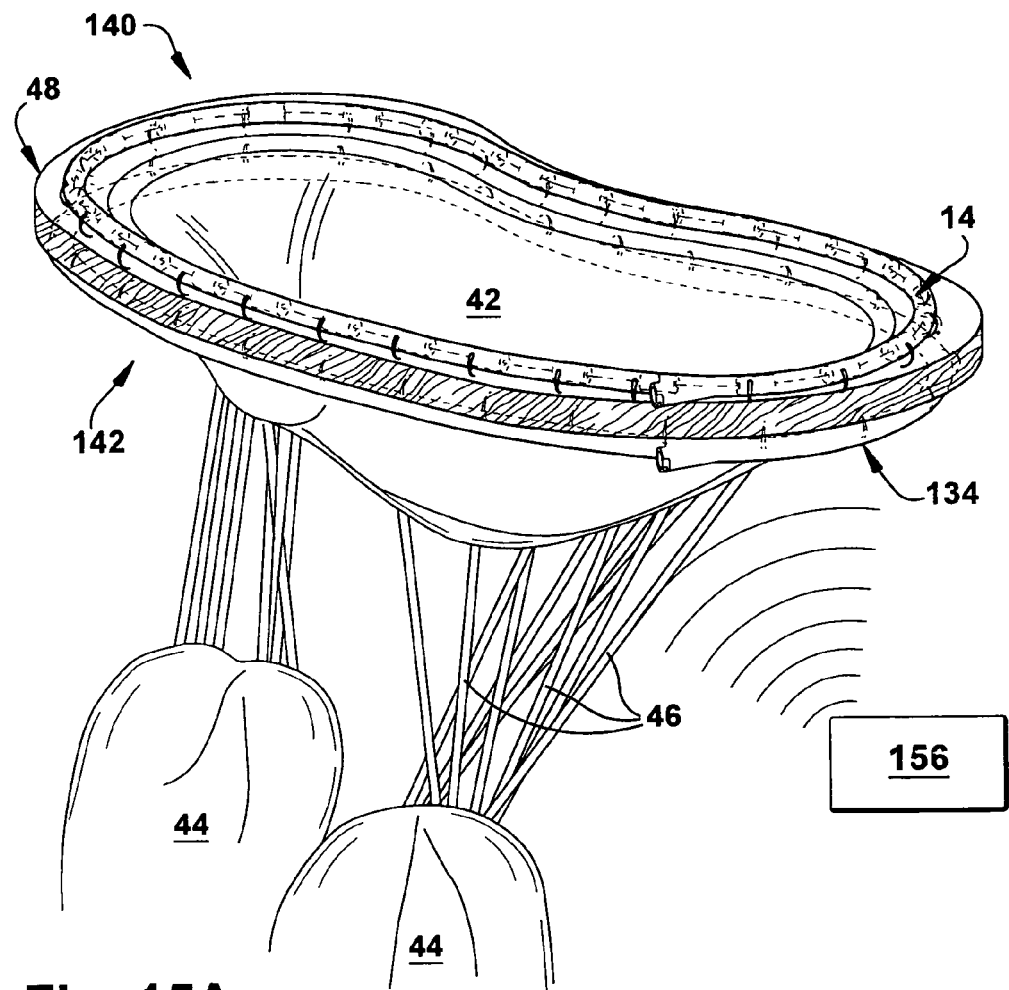
FIG. 15A is a perspective view showing of the apparatus in FIG. 14A in a tensioned configuration secured to the superior aspect of the regurgitant mitral valve.
Figure 15B:
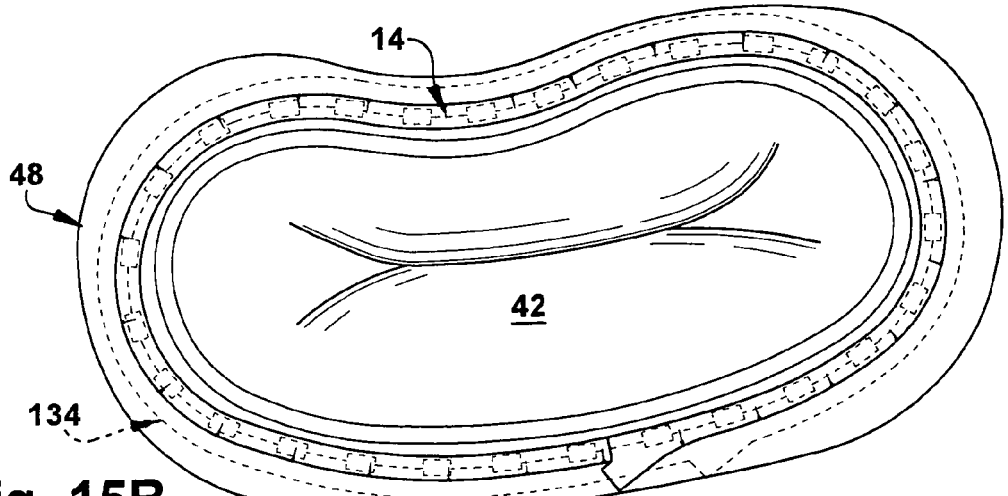
FIG. 15B is a plan view showing the apparatus of FIG. 15A secured to the superior aspect of the regurgitant mitral valve.
Figure 16:
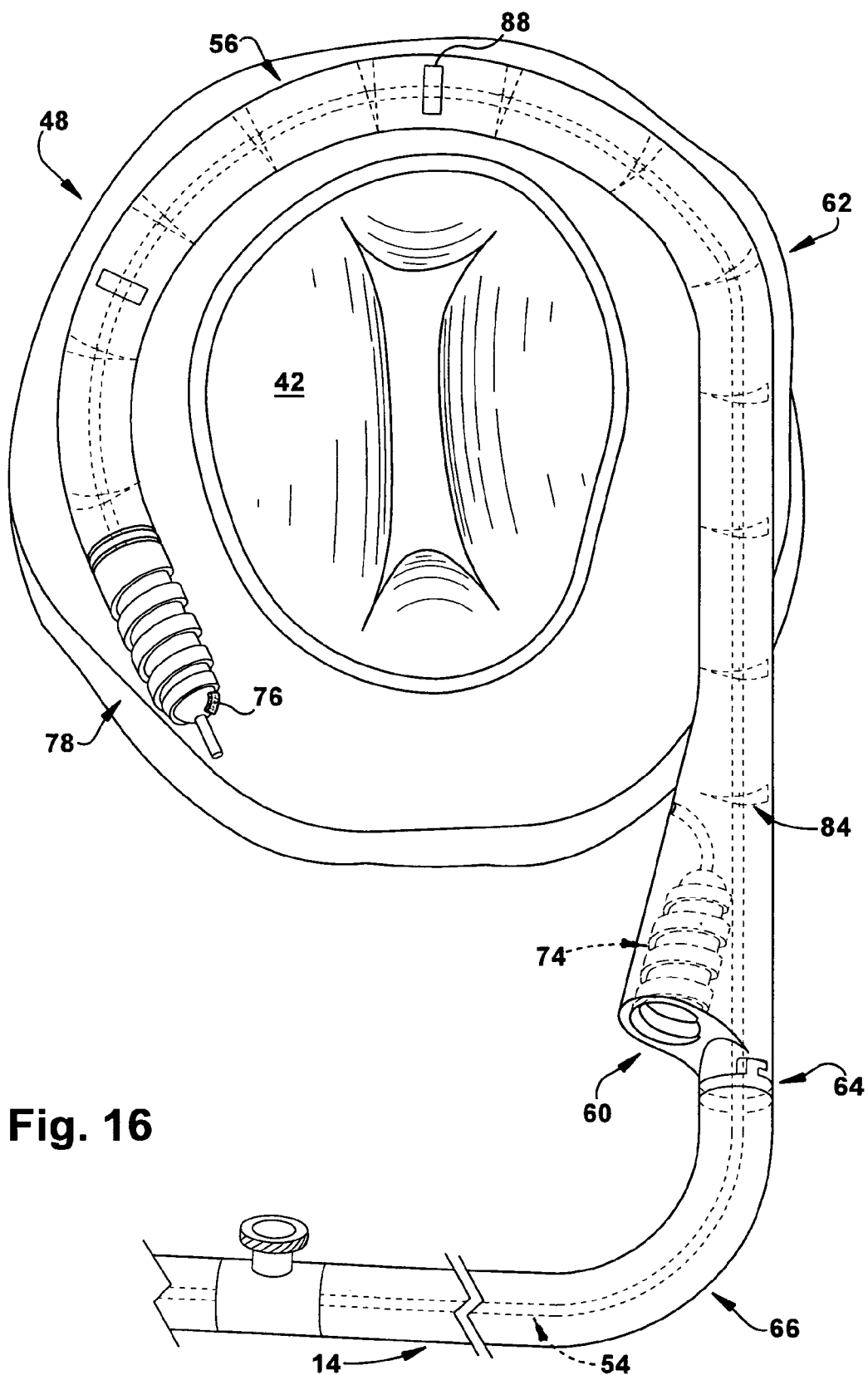
FIG. 16 is a perspective view showing the apparatus of FIG. 3 secured to the superior aspect of the regurgitant mitral valve annulus.
Figure 17:
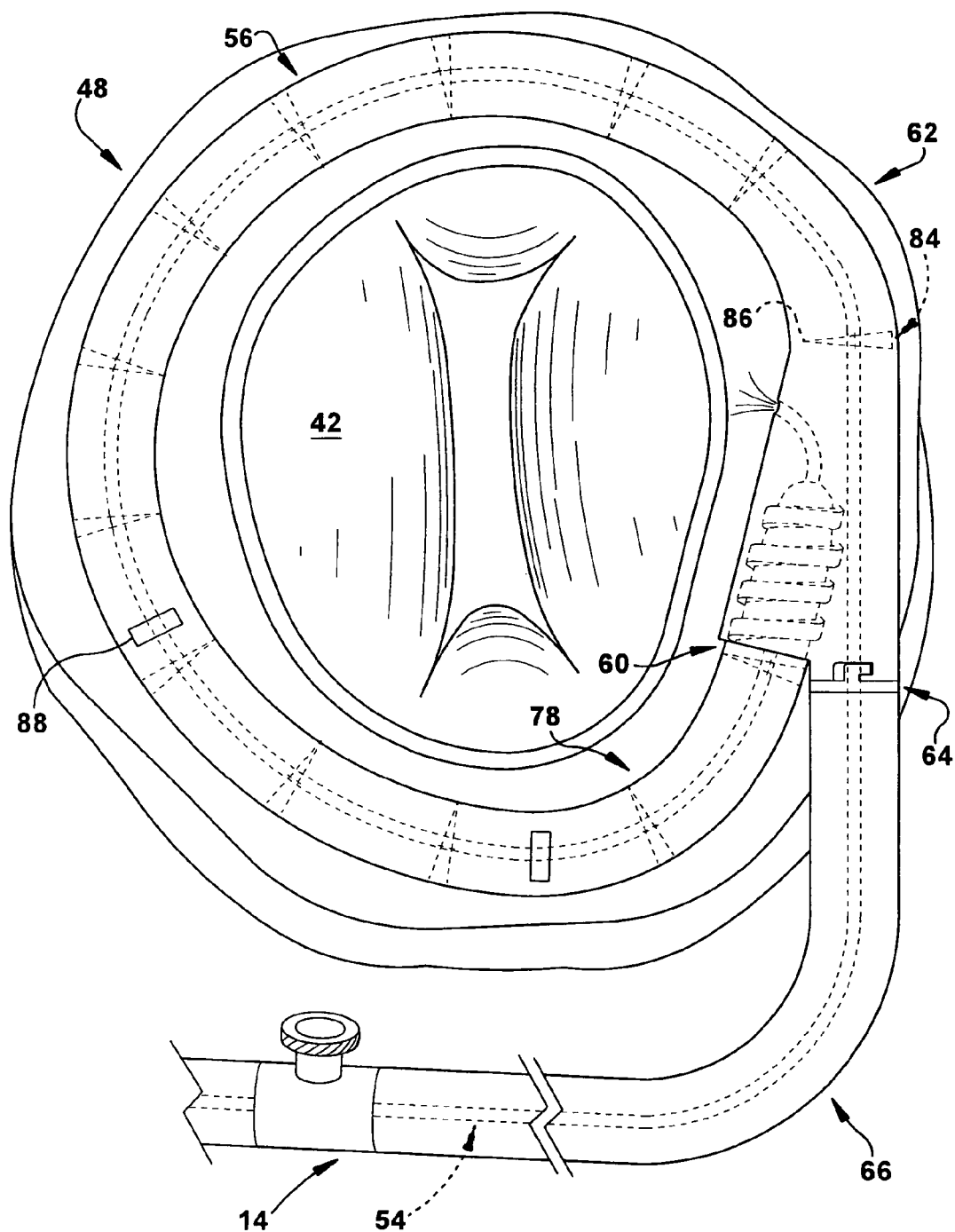
FIG. 17 is a perspective view showing the apparatus of FIG. 16 secured to the superior aspect of the regurgitant mitral valve annulus and formed into a completed annuloplasty ring.

After the distal end portion 56 of each of the first and second annuloplasty rings 14 and 134 are respectively secured about the superior and inferior aspects 140 and 142 of the mitral valve annulus 48, an electromagnetic wire 148 may be inserted into the first annuloplasty ring as shown in FIGS. 14A and 14B. When the electromagnetic wire 148 is appropriately positioned in the first annuloplasty ring 14, electromagnetic energy (e.g., RF energy) may be delivered to the electromagnetic wire (FIGS. 15A and 15B). Delivery of RF energy adjusts the electromagnetic wire 148 from the first relaxed configuration to the second tensioned configuration as described above. When the electromagnetic wire 148 obtains the second tensioned configuration, the diameter of the distal end portion 56 of the first annuloplasty ring 14 is reduced so that the mitral leaflets properly coapt and regurgitation of blood flow through the mitral valve 42 is reduced or eliminated (FIGS. 15A and 15B). The proximal end portion 150 of the electromagnetic wire 148 and the main body portion 66 of the first annuloplasty ring 14 may then be retracted and the procedure completed as described above.

Another embodiment of the present invention is illustrated in FIGS. 25A-27. The apparatus $10_b$ is identically constructed as the apparatus 10 shown in FIG. 1, except where as described below. In FIG. 25A-27, structures that are identical as structures in FIG. 1 use the same reference numbers, whereas structures that are similar but not identical carry the suffix "b".

Figure 25A:
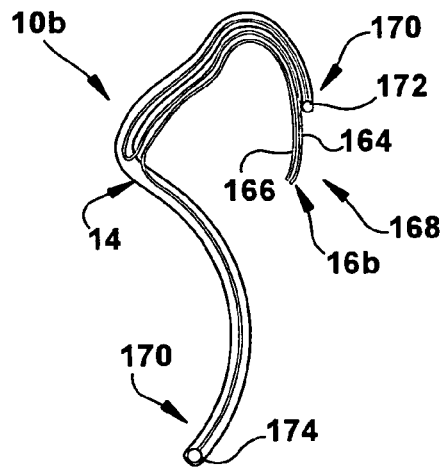
FIG. 25A is a cross-sectional view showing an alternative embodiment of the apparatus shown in FIG. 13 having a flexible configuration.
Figure 25B:
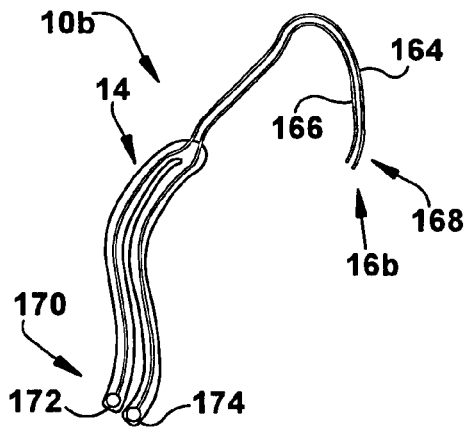
FIG. 25B is a cross-sectional view showing the apparatus of FIG. 25A in an alternative configuration.

An apparatus $10_b$ for modifying the annulus 18 of a cardiac valve 12 to reduce regurgitation of blood flow through the cardiac valve comprises a first annuloplasty ring 14 (FIG. 3) and an elongate flexible body $16_b$ (FIGS. 25A and 25B). The elongate flexible body $16_b$ can comprise first and second wires 164 and 166 having proximal and distal end portions 168 and 170. The first and second wires 164 and 166 can be made of a flexible or semi-rigid material such as stainless steel, Nitinol, titanium, plastic polymer, or the like. The first and second wires 164 and 166 may be made from a shape memory alloy or, alternatively, from a ferromagnetic material (as described above). The distal end portion 170 of each of the first and second wires 164 and 166 may respectively include first and second magnetic members 172 and 174. The first and second magnetic members 172 and 174 may be identically constructed as the magnetic members 154 described above.

Figure 26A:
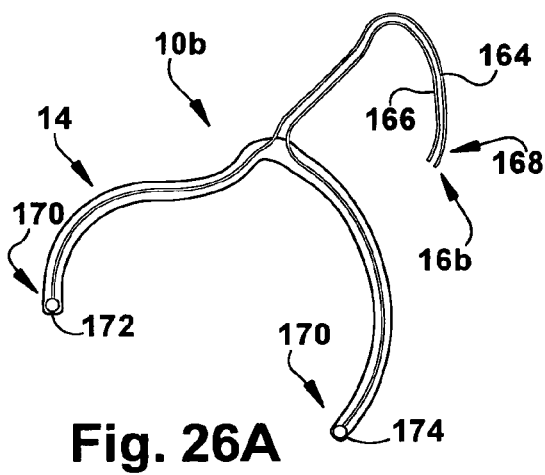
FIG. 26A is a cross-sectional view showing the apparatus shown in FIG. 25A having a semi-flexible configuration.
Figure 26B:
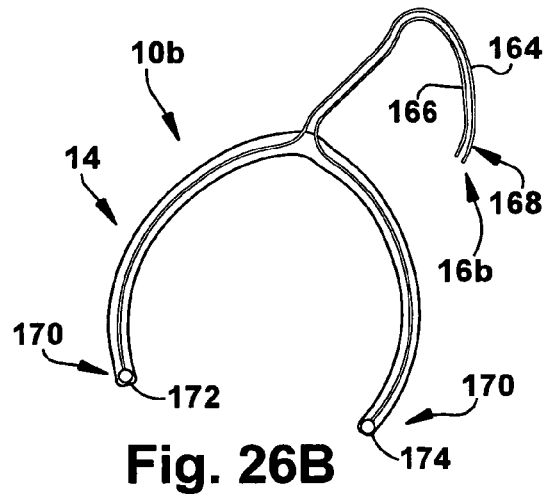
FIG. 26B is a cross-sectional view showing the apparatus in FIG. 25B having a semi-flexible configuration.

As shown in FIGS. 25A and 25B, the first and second wires 164 and 166 may be inserted into the first annuloplasty ring 14 in a first relaxed configuration. More particularly, the distal end portion 170 of the first wire 164 may be positioned at the terminal end 58 of the first annuloplasty ring 14, and the distal end portion of the second wire 166 may be positioned near the means for disconnecting 64 of the first annuloplasty ring. As described above, the distal end portion 56 of the first annuloplasty ring 14 may then be coupled around the superior aspect 140 of the mitral annulus 48, for example, by urging the terminal end 58 towards the receptacle portion 74 of the first annuloplasty ring (FIGS. 26A and 26B).

Figure 27:
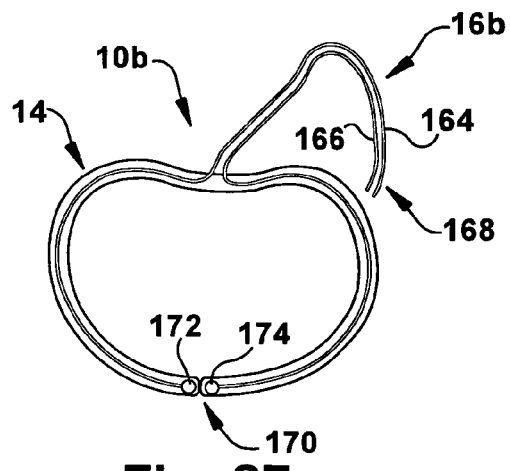
FIG. 27 is a cross-sectional view showing the apparatus in FIG. 26A having a rigid configuration.

When the terminal end 58 and the receptacle portion 74 of the first annuloplasty ring 14 are positioned near one another, the first and second magnetic members 172 and 174 are respectively attracted to one another and pull the terminal end and the receptacle portion together. The distal end portion 56 of the first annuloplasty ring 14 may now encircle the superior aspect 140 of the mitral valve annulus 48, and the deployable hook members 86 deployed (as described above) to secure the distal end portion. Next, the proximal end portion 168 of each of the first and second wires 164 and 166 may be manipulated so that the first and second wires obtain the second tensioned configuration (FIG. 27). For example, the proximal end portion 168 of each of the first and second wires 164 and 166 may be withdrawn so that the distal end portion 56 of the first annuloplasty ring 14 is tightened, thus causing the mitral leaflets to coapt properly and reduce or eliminate regurgitation of blood flow through the mitral valve 42. Alternatively, the flexible body 90 may be used to ensnare a portion of the first and second wires 164 and 166 and then manipulated to withdraw the first and second wires.

After the distal end portion 56 of the first annuloplasty ring 14 is appropriately adjusted and regurgitation of blood flow through the mitral valve 42 is reduced or eliminated, the proximal end portion 168 of each of the first and second wires 164 and 166 may be disconnected from the distal end portion 170 of each of the first and second wires and retracted from the vasculature of the patient. Additionally, the main body portion 66 of the first annuloplasty ring 14 may be disconnected from the distal end portion 56 and also retracted from the vasculature of the patient From the above description of the invention, those skilled in the art will perceive improvements, changes and modifications. For example, the present invention may be placed via a minimally invasive, transthoracic approach via a port on the heart wall or, alternatively, via an open-chest procedure under direct supervision. Additionally, it will be appreciated that the present invention can be used to modify the annulus of other cardiac valves, such as the tricuspid and aortic valves 40 and 38. Such improvements, changes and modifications within the skill of the art are intended to be covered by the appended claims.

Having described the invention, we claim:

1. An apparatus for modifying the annulus of a cardiac valve to reduce regurgitation of blood flow through the cardiac valve, said apparatus comprising:
   a first annuloplasty ring having a first diameter and being disposed about a first aspect of the annulus of the cardiac valve, said first annuloplasty ring including a terminal end and a connecting section spaced apart by a predetermined length, said connecting section including a means for disconnecting from a main body portion and a receptacle portion adapted to receive and interconnect with said terminal end; and
   an elongate flexible body comprising proximal and distal end portions and being insertable into said first annuloplasty ring, said elongate flexible body including an adjustable mechanism for selectively adjusting said elongate flexible body from a first relaxed configuration to a second tensioned configuration;
   said first annuloplasty ring being adaptable to obtain a second smaller diameter and to cause the annulus of the cardiac valve to be modified and reduce regurgitation of blood flow through the cardiac valve when said elongate flexible body obtains said second tensioned configuration.

2. The apparatus of claim 1, wherein said adjustment mechanism is manually manipulated so that said elongate flexible body obtains said second tensioned configuration.

3. The apparatus of claim 1, wherein said adjustment mechanism is electromagnetically manipulated so that said elongate flexible body obtains said second tensioned configuration.

4. The apparatus of claim 1, wherein a second annuloplasty ring is disposed about a second aspect of the annulus of the cardiac valve, said second annuloplasty ring being magnetically coupled to said first annuloplasty ring to secure said first annuloplasty ring about the first aspect of the annulus of the cardiac valve.

5. The apparatus of claim 1, wherein a positioning catheter is used to magnetically guide said first and/or second annuloplasty rings to the first and/or second aspects of the annulus of the cardiac valve, respectively.

6. The apparatus of claim 1, wherein said distal end portion of said first annuloplasty ring includes a plurality of deployable hook members.

7. The apparatus of claim 1, wherein said terminal end has a threaded portion for mating with said receptacle portion, said receptacle portion including a threaded portion that is complementary in shape to said terminal end.

8. An apparatus for modifying the annulus of a cardiac valve to reduce regurgitation of blood flow through the cardiac valve, said apparatus comprising:
a first annuloplasty ring having a first diameter and being disposed about a first aspect of the annulus of the cardiac valve, said first annuloplasty ring including a terminal end and a connecting section spaced apart by a predetermined length, said connecting section including a means for disconnecting from a main body portion and a receptacle portion adapted to receive and interconnect with said terminal end; and
a flexible body comprising first and second oppositely disposed strut members having proximal and distal end portions and a cinching mechanism for adjusting said flexible body from a first relaxed configuration to a second tensioned configuration, said cinching mechanism being operatively connected to said distal end portion of said strut members;
said cinching mechanism comprising a resistance member operatively coupled to said distal end portion of said strut members and a harness member operatively coupled to a pull wire extending between said strut members;
said flexible body being disposed in a delivery catheter being insertable into said first annuloplasty ring, said delivery catheter comprising proximal and distal end portions and an opening at said distal portion for extending said harness member therethrough;
said flexible body being adaptable to obtain said second tensioned configuration and to cause said first annuloplasty ring to obtain a second smaller diameter so that the annulus of the cardiac valve is modified and regurgitation of blood flow through the cardiac valve is reduced.

9. The apparatus of claim 8, wherein a second annuloplasty ring is disposed about a second aspect of the annulus of the cardiac valve, said second annuloplasty ring being magnetically coupled to said first annuloplasty ring so that said first annuloplasty ring is secured to the first aspect of the annulus of the cardiac valve.

10. The apparatus of claim 8, wherein a positioning catheter is used to magnetically guide said first and/or second annuloplasty rings to the first and/or second aspects of the annulus of the cardiac valve, respectively.

11. An apparatus for modifying the annulus of a cardiac valve to reduce regurgitation of blood flow through the cardiac valve, said apparatus comprising:
a first annuloplasty ring having a first diameter and being disposed about a first aspect of the annulus of the cardiac valve, said first annuloplasty ring including a terminal end and a connecting section spaced apart by a predetermined length, said connecting section including a means for disconnecting from a main body portion and a receptacle portion adapted to receive and interconnect with said terminal end; and
an electromagnetic wire having proximal and distal end portions, said electromagnetic wire including a plurality of magnetic members operably connected to said electromagnetic wire and an adjustable mechanism for selectively adjusting said electromagnetic wire from a first relaxed configuration to a second tensioned configuration, said electromagnetic wire being insertable into said first annuloplasty ring;
said adjustable mechanism being selectively adjustable so that said first annuloplasty ring is adaptable to obtain a second smaller diameter and modify the annulus of the cardiac valve to reduce regurgitation of blood flow through the cardiac valve.

12. The apparatus of claim 11, wherein a second annuloplasty ring is disposed about a second aspect of the annuloplasty ring, said second annuloplasty ring being magnetically coupled to said first annuloplasty ring so that said first annuloplasty ring is secured to the first aspect of the annulus of the cardiac valve.

13. The apparatus of claim 12, wherein a positioning catheter is used to magnetically guide said first and/or second annuloplasty rings to the first and/or second aspects of the annulus of the cardiac valve, respectively.

* * * * *